(12) United States Patent
Phillips et al.

(10) Patent No.: US 12,362,070 B2
(45) Date of Patent: Jul. 15, 2025

(54) SYSTEMS AND METHODS FOR PREDICTING OUTCOMES OF BURN PATIENTS

(71) Applicant: BData, Inc., Edina, MN (US)

(72) Inventors: Bartholomew Phillips, Edina, MN (US); Erica Murata, Chicago, IL (US); Matthew Phillips, Apex, NC (US)

(73) Assignee: BData, Inc., Edina, MN (US)

( * ) Notice: Subject to any disclaimer, the term of this patent is extended or adjusted under 35 U.S.C. 154(b) by 193 days.

(21) Appl. No.: 18/131,666

(22) Filed: Apr. 6, 2023

(65) Prior Publication Data

US 2023/0326606 A1 Oct. 12, 2023

Related U.S. Application Data

(60) Provisional application No. 63/328,203, filed on Apr. 6, 2022.

(51) Int. Cl.
*G16H 50/30* (2018.01)
*G16H 40/20* (2018.01)
*G16H 50/20* (2018.01)

(52) U.S. Cl.
CPC ............. *G16H 50/30* (2018.01); *G16H 40/20* (2018.01); *G16H 50/20* (2018.01)

(58) Field of Classification Search
CPC ........ G16H 10/20; G16H 10/40; G16H 10/60; G16H 10/65; G16H 15/00; G16H 20/10; G16H 20/13; G16H 20/17; G16H 20/30; G16H 20/40; G16H 20/60; G16H 20/70; G16H 20/90; G16H 30/20; G16H 30/40;
(Continued)

(56) References Cited

U.S. PATENT DOCUMENTS 9,272,090 B2 3/2016 Salinas et al.
10,783,632 B2 9/2020 Fan et al.
(Continued)

OTHER PUBLICATIONS

"DALEX: moDel Agnostic Language for Exploration and explanation", accessed at https://github.com/ModelOriented/DALEX on Jun. 30, 2023, 6 pages.
(Continued)

*Primary Examiner* — Chad A Newton
(74) *Attorney, Agent, or Firm* — Barnes & Thornburg LLP

(57) ABSTRACT

The disclosed technology includes a method for determining outcomes of patients across healthcare centers, the method including: receiving, at a computer system, patient data for patients in healthcare centers, training, using machine learning techniques and a portion of the data for the burn patients, a predictive model to predict patient outcomes based on assessing patient data for patients across the healthcare centers, and returning the trained predictive model for runtime use. During runtime use, the method can include: providing the patient data as input to the predictive model, receiving, as output, predicted patient outcomes for at least one patient amongst the patients in the healthcare centers, generating, based on the predicted patient outcomes, at least one care recommendation, generating output representative of the predicted patient outcomes and the care recommendation, and transmitting the output to a user computing device for presentation in a graphical user interface (GUI) display.

20 Claims, 43 Drawing Sheets

(58) Field of Classification Search
CPC ........ G16H 40/20; G16H 40/40; G16H 40/60;
G16H 40/63; G16H 40/67; G16H 50/20;
G16H 50/30; G16H 50/50; G16H 50/70;
G16H 50/80; G16H 70/20; G16H 70/40;
G16H 70/60; G16H 80/00
See application file for complete search history.

(56) References Cited

U.S. PATENT DOCUMENTS

| | | | |
|---|---|---|---|
| 11,337,643 | B2 | 5/2022 | Fan et al. |
| 2019/0272922 | A1* | 9/2019 | Albright .................. G06N 3/04 |
| 2020/0038587 | A1 | 2/2020 | Hahn et al. |
| 2020/0401917 | A1* | 12/2020 | Daware ................ G06F 16/242 |
| 2021/0272701 | A1 | 9/2021 | Jones |
| 2022/0301711 | A1* | 9/2022 | Rashidi .................. G16H 50/30 |
| 2023/0298751 | A1* | 9/2023 | Taoka .................... G16H 50/70 |
| | | | 705/2 |

OTHER PUBLICATIONS

"Lime: Explaining the predictions of any machine learning classifier", posted Jul. 29, 2021 and accessed at https://github.com/marcotcr/lime on Jun. 30, 2023, 5 pages.

Bloemsma, GC et al. "Mortality and causes of death in a burn centre", Burns. 2008;34(8):1103-7.

Dokter J et al., "External validation of the revised Baux score for the prediction of mortality in patients with acute burn injury", J Trauma Acute Care Surg. 2014;76(3):840-5.

Gillespie, R., et al., Diagnosis-related groupings (DRGs) and wound closure: roundtable discussion. J Burn Care Rehabil, 1987. 8(3): pp. 199-209.

Harris, C.R. et al. "Array programming with NumPy", Nature (2020) 585, 357-362.

Hilton, C. Beau et al., "Personalized predictions of patient outcomes during and after hospitalization using artificial intelligence", Digital Medicine (2020)3:51: pp. 1-8.

Hussain A et al., "Predicting survival in thermal injury: a systematic review of methodology of composite prediction models", Burns 2013;39(5):835-50.

Johnson, L.S., et al., Hospital Length of Stay—Does 1% TBSA Really Equal 1 Day? Journal of Burn Care & Research, 2011. 32(1): pp. 13-19.

Koo, Boo San et al., "Machine learning model for identifying important clinical features for predicting remission in patients with rheumatoid arthritis treated with biologics", Arthritis Research & Therapy (2021) 23:178, pp. 1-10.

Lauritsen, Simon M. et al., "Explainable artificial intelligence model to predict acute critical illness from electronic health records", Nature Communications (2020)11:3852: pp. 1-11.

Minne L et al., "Effect of changes over time in the performance of a customized SAPS-II model on the quality of care assessment", Intensive Care Med. 2012;38(1):40-6.

Pedregosa, Fabian et al., "Scikit-learn: Machine Learning in Python", 2011 12(85): pp. 2825-2830.

Pereira, C et al., "Outcome measures in burn care. Is mortality dead?", Burns 2004;30(8):761-71.

Prokhorenkova, Lludmilla et al., "CatBoost: unbiased boosting with categorical features", arXiv:1706.09516v5 [cs.LG] Jan. 20, 2019: pp. 1-23.

Schomaker, M et al., "Bootstrap Inference when Using Multiple Imputation", Statistics in Medicine. 2018;37 (14):2252-2266.

Sheppard, NN et al., Prognostic scoring systems in burns: a review. Burns. 2011;37(8):1288-95.

Smith, Matthew et al., ""Identifying mortality factors from Machine Learning using Shapley values—a case of COVID19"", Expert Systems With Applications 176 (2021) 114832: pp. 1-12.

Steinvall I et al., "Standardised mortality ratio based on the sum of age and percentage total body surface area burned is an adequate quality indicator in burn care: An exploratory review", Burns. 2016;42(1):28-40.

Taylor, S.L., et al., Not all patients meet the 1day per percent burn rule: A simple method for predicting hospital length of stay in patients with burn. Burns, 2017. 43(2): pp. 282-289.

Taylor, SL et al., "A validity review of the National Burn Repository", J Burn Care Res. 2013;34(2):274-80.

Thorsen-Meyer, Hans-Christian et al., "Dynamic and explainable machine learning prediction of mortality in patients in the intensive care unit: a retrospective study of high-frequency data in electronic patient records", Lancet Digital Health Mar. 12, 2020 2: pp. e179-e191.

Virtanen, Pauli et al., SciPy 1.0: Fundamental Algorithms for Scientific Computing in Python. Nature Methods (2020), 17(3), pp. 261-27.

\* cited by examiner

700

| Variable | Pct Missing |
|---|---|
| Age | 0 |
| Age squared | 0 |
| Tbsa | 18 |
| Inhalation | 8 |
| Sex | 0 |
| Respiratory Failure | 0 |
| Injury Circumstance | 4 |
| Homeless | 1 |
| Race | 5 |
| Interfacility Transfer | 3 |
| Marital status | 20 |

| Variable | Pct Missing |
|---|---|
| Etiology | 8 |
| 3rd degree burn | 0 |
| Payor | 5 |
| Living Situation | 4 |
| Living with | 23 |
| Alcohol | 13 |
| Drugs | 11 |
| Procedures | 0 |
| Comorbidities | 0 |
| Infection | 0 |
| Volume | 0 |

710

| Variable | Accuracy | F1 | KID rate | N |
|---|---|---|---|---|
| inh_inj | 0.963360708 | 0.804468013 | 0.892175381 | 6332 |
| inj_circ | 0.343891403 | 0.112584853 | -1.664294761 | 2652 |
| race | 0.616480554 | 0.122244536 | 0.308333838 | 2597 |
| iftd | 0.215085639 | 0.126802773 | -0.195228812 | 3036 |
| marital | 0.729644451 | 0.260701976 | 0.896477526 | 12994 |
| etio | 0.235588972 | 0.071194007 | 0.250333893 | 4389 |
| inj_x_rf | 0.995420088 | 0.960960307 | 0.997713012 | 6332 |
| pay | 0.190105263 | 0.08996631 | 0.545843237 | 14250 |
| live_situ | 0.744680851 | 0.235625 | 0.897292471 | 94 |
| live_with | 0.383707944 | 0.242608703 | 0.470834233 | 14326 |
| alcohol | 0.762834756 | 0.318266878 | 0.374795585 | 8551 |
| drugs | 0.772634445 | 0.315651674 | 0.36762323 | 7345 |

| Variable | Pearson r | Spearman's rho | N |
|---|---|---|---|
| tbsa | 0.458259151 | 0.425370884 | 12225 |
| los | 0.648892022 | 0.634244735 | 1344 |

| Variable | Feature Importance |
|---|---|
| TBSA (total body surface area) | 21.889 |
| Age | 15.896 |
| Age squared | 9.322 |
| Respiratory Failure | 8.871 |
| Inhalation injury | 8.263 |
| Burn etiology | 7.488 |
| Number of procedures | 7.437 |
| Facility volume | 6.849 |
| 3rd degree burn present | 3.314 |
| Number of comorbidities | 2.308 |
| Who patient lives with | 1.246 |
| Gender | 1.153 |
| Primary method of payment | 1.081 |
| Injury Circumstance | 1.047 |
| Alchohol status | 0.867 |
| Inhalation injury and respiratory failure combined | 0.795 |
| Race | 0.635 |
| Inter-facility transfer detail | 0.510 |
| Drug Status | 0.481 |
| Marital status | 0.273 |
| Living situation | 0.265 |
| Presence of infection | 0.010 |

730

| Variable | Feature Importance |
|---|---|
| Number of procedures | 22.635 |
| TBSA (total body surface area) | 20.513 |
| Facility volume | 18.618 |
| Respiratory Failure | 6.525 |
| 3rd degree burn present | 6.515 |
| Burn etiology | 4.567 |
| Age squared | 4.466 |
| Age | 3.286 |
| Number of comorbidities | 3.069 |
| Primary method of payment | 1.696 |
| Drug Status | 1.558 |
| Race | 1.117 |
| Living situation | 0.828 |
| Injury Circumstance | 0.828 |
| Who patient lives with | 0.800 |
| Inhalation injury | 0.742 |
| Inter-facility transfer detail | 0.661 |
| Alchohol status | 0.479 |
| Inhalation injury and respiratory failure combined | 0.414 |
| Marital status | 0.392 |
| Gender | 0.195 |
| Presence of infection | 0.095 |

SELECTED BURN INJURIES
*HOVER over the icon to learn more about each specific burn case*

| Years | TBSA | Inhalation Injury | Discharge Disposition | Patient Sex | Predicted Outcome | Actual Outcome | |
|---|---|---|---|---|---|---|---|
| 2016 | 19 | No | Deceased/Expired | Male | Predicted.. | Deceased | ⓘ |
| 2016 | 19 | No | Deceased/Expired | Male | Predicted.. | Deceased | ⓘ |
| 2016 | 5 | No | Deceased/Expired | Male | Predicted.. | Deceased | ⓘ |
| 2017 | 26.5 | No | Deceased/Expired | Male | Predicted.. | Deceased | ⓘ |
| 2017 | 11.25 | No | Deceased/Expired | Male | Predicted.. | Deceased | ⓘ |
| 2018 | 12.25 | No | Deceased/Expired | Male | Predicted.. | Deceased | ⓘ |
| 2019 | 84.5 | No | Deceased/Expired | Male | Predicted.. | Deceased | ⓘ |

INJURY DETAIL

- Admission Year: 2015
- Total Burn Surface Area: 15
- Inhalation Injury: Not known/Not recorded
- Discharge Disposition: Deceased/Expired
- Injury Circumstance: Accidental Injury: Non-Employer
- Place of Occurrence:

OUTCOMES

- Predicted Outcomes: 0.2550 (Predicted survival)
- Actual Outcome: Deceased

ADMISSION & TREATMENT DETAIL

- Admission Category: Acute
- Admission Source: Direct from Scene of Injury
- Admission Type: Initial admission
- Days Ventilator: 6
- Etiology Category: Scald
- Care Directive Applied: Treatment withdrawn
- Inter Facility Transfer Detail: Not Referred/Transferred From
- Transport Modes: Ground Ambulance

PATIENT DETAIL

- Patient Sex: Female
- Age in Years: 83
- Ethnicity (Race): Not Hispanic or Latino (Black or
- Marital Status: Single
- Patient Living With: Other Family Member
- Home Residence Type: House/Apartment
- Alternate Home Residence:

FIG. 12C (Cont'd)

FIG. 15E

SYSTEMS AND METHODS FOR PREDICTING OUTCOMES OF BURN PATIENTS

INCORPORATION BY REFERENCE

This application claims priority to U.S. Provisional Application Ser. No. 63/328,203, filed on Apr. 6, 2022, the disclosure of which is incorporated by reference in its entirety.

TECHNICAL FIELD

This document describes systems, methods, and computer modeling techniques for automatically performing risk-based patient outcome assessments using patient data, such as determining mortality and length of stay metrics in healthcare settings for burn patients.

BACKGROUND

Burn care centers may experience varying degrees of mortality and length of stay (LOS) outcomes for their patients. The mortality and/or LOS outcomes can be patient-specific. The mortality and LOS outcomes may also impact quality of care to the patients of the burn care centers. Assessing the mortality and LOS outcomes at burn care centers can improve patient outcomes. Mortality is a common outcome that can be assessed at a healthcare center to determine how to improve quality of care at that center. LOS after burn injuries can also be assessed to determine quality of care at the particular center. Traditionally, patients can be quoted an estimate of 1 day per % total burn surface area (TBSA) as their LOS. This quote, however, is not the same for many patients or cohorts of patients. Moreover, the quote can be center-dependent.

SUMMARY

In general, this document describes technology for determining burn patient outcomes, such as burn patient mortality information and LOS information, based on burn patient data, including generating patient-specific insights regarding possible outcomes, optimal treatments, relative performance of burn centers, and other details. Accordingly, the disclosed technology can provide a reliable, risk-adjusted statistical model of mortality, LOS, and other types of patient outcomes based by leveraging current and historical patient data from various geographically-distributed healthcare centers (e.g., burn centers). The modeling described herein can be used to not only determine and recommend patient care solutions, but also provide for reasonable comparison of various patient outcomes across the different healthcare centers, address data integrity and completeness, and provide metrics that the healthcare centers can use for identifying healthcare quality issues. The disclosed technology can be implemented on any of a variety of appropriate computer systems, such as computer server systems (e.g., cloud computer systems), client computing devices (e.g., laptops, smartphones, tablets), computer networks (e.g., internet, WAN, LAN, VPN), and/or combinations thereof. The disclosed technology can include systems for obtaining anonymized burn patient data (e.g., data for patients who have suffered and been treated for a burn injury, such as at a specialized treatment center for treating burn patients), training one or more models using at least a portion of the anonymized burn patient data, and using the one or more models to determine one or more insights, such as determining projected outcomes for burn patients (e.g., determining burn patient mortality), assessing performance of specialized burn treatment centers, determining burn treatments to be used for particular burn patients, and/or other information. Such insights can be used, for example, prospectively by physicians and other medical personnel to provide treatment of current burn patients. Such insights can, additionally and/or alternatively, be used retrospectively to evaluate compare the performance, treatment algorithms, patient outcomes, and/or personnel at different burn treatment centers. Other uses are also possible.

The disclosed technology may also be used by individual burn care centers to assess their quality of care against other burn care centers, and thus drive quality improvements in provided healthcare. Burn care centers can benefit from driving quality of care and improved outcomes through collection and sharing of clinical data using clinical registries. Accordingly, the disclosed technology can provide for comparison of various patient outcomes at different healthcare centers, risk-adjusted quality assessments, and improvement models to measure healthcare center performance and quality of care. The disclosed technology can also be used to generate recommended improvements to the performance and quality of care provided by the healthcare centers.

One or more embodiments described herein can include a method for determining outcomes of patients across a plurality of healthcare centers, the method including: receiving, at a computer system, patient data for patients in a group of healthcare centers, training, at the computer system and using (i) one or more machine learning techniques and (ii) at least a portion of the data for the burn patients, a predictive model, the predictive model being trained to predict patient outcomes based on assessing a group of patient data for a group of patients across the group of healthcare centers, and returning, at the computer system, the trained predictive model for runtime use. During the runtime use, the method further can include: providing the patient data for the patients in the group of healthcare centers as input to the predictive model, receiving, as output from the predictive model, predicted patient outcomes for at least one patient amongst the patients in the group of healthcare centers, generating, based at least in part on the predicted patient outcomes, at least one care recommendation, generating output representative of the predicted patient outcomes and the at least one care recommendation, and transmitting the output to a user computing device for presentation in a graphical user interface (GUI) display.

In some implementations, the embodiments described herein can optionally include one or more of the following features. The patients can be burn patients. The predictive model can be a gradient boosted regression model. The predictive model can be a CatBoost model. The predicted patient outcomes can include a predicted risk of mortality for the at least one patient. The predicted patient outcomes may include a predicted length of stay (LOS) for the at least one patient. The predicted patient outcomes may include a predicted recovery rate for the at least one patient. The at least one care recommendation can be a patient-specific treatment or care plan. The at least one care recommendation can be a healthcare center-specific care plan.

In some implementations, the method can also include processing, at the computer system, based on: de-identifying the received data, splitting the de-identified data into a training dataset and a testing dataset, scaling one or more continuous variables in the training dataset, removing a predetermined quantity of sigma outliers from the training dataset, imputing missed data in the training dataset, and returning the training dataset for the training. The de-identified data can be split into the training dataset and the testing dataset based on a predetermined temporal limitation, the predetermined temporal limitation being a range of years that the received data was collected.

In some implementations, the at least one care recommendation can include a performance rating for one or more of the group of healthcare centers. The method can also include determining and comparing, at the computer system, the performance rating for the one or more of the plurality of healthcare centers, and generating, at the computer system, output for presenting the comparison for the one or more of the group of healthcare centers. Sometimes, comparing, at the computer system, the performance rating for the one or more of the group of healthcare centers can include identifying one or more factors of high performing healthcare centers that are different from low performing healthcare centers.

As another example, the predicted patient outcomes can include a predicted risk of mortality for a cohort of the patients. The predicted patient outcomes can include a predicted length of stay (LOS) for a cohort of the patients. The predicted patient outcomes can include a predicted recovery rate for a cohort of the patients.

In yet some implementations, training the predictive model further can include: determining feature importance values for variables in the portion of the data for the burn patients using CatBoost feature selection modeling techniques, and identifying a portion of the variables having respective feature importance values that exceed a threshold feature importance level. The identified portion of the variables can have a greater effect on output from the predictive model than other variables having respective feature importance values that are less than the threshold feature importance level. The identified portion of the variables can include at least total body surface area (TBSA) and age. The method can also include generating output representative of the portion of the variables having respective feature importance values that exceed the threshold feature importance level, and transmitting the output representative of the portion of the variables to the user computing device for presentation in the GUI display.

One or more embodiments described herein can include a computing system for determining outcomes of patients across a group of healthcare centers, the computing system including: one or more processors, and one or more storage devices storing instructions that, when executed by the one or more processors, cause the one or more processors to perform operations including: receiving patient data for patients in a group of healthcare centers, training, using (i) one or more machine learning techniques and (ii) at least a portion of the data for the burn patients, a predictive model, the predictive model having been trained to predict patient outcomes based on assessing a group of patient data for a group of patients across the group of healthcare centers, and returning the trained predictive model for runtime use. During the runtime use, the operations further can include: providing the patient data for the patients in the group of healthcare centers as input to the predictive model, receiving, as output from the predictive model, predicted patient outcomes for at least one patient amongst the patients in the group of healthcare centers, generating, based at least in part on the predicted patient outcomes, at least one care recommendation, generating output representative of the predicted patient outcomes and the at least one care recommendation, and transmitting the output to a user computing device for presentation in a graphical user interface (GUI) display.

The system can optionally include one or more of the above-mentioned features.

The devices, system, and techniques described herein may provide one or more of the following advantages. For example, risk-adjusted benchmarking and model analysis can provide robust quality improvement identification and recommendations for various healthcare centers. Patient outcomes can be evaluated across a variety of healthcare centers and used to automatically identify opportunities for improvement in one or more particular healthcare centers. The disclosed modeling techniques may also be applied to various different types of key outcome measures to assess quality of care and areas for improvement at healthcare centers that service different types of patient needs, not just burn care.

As another example, the disclosed technology can provide technical solutions to technical problems, such as through the use of gradient boosted regression modeling to provide greater model precision and sensitivity regarding sparse burn patient training datasets that may otherwise be difficult or challenging to use to accurately train usable models. The modeling used can also be iterative and allow for continuous refinement to improve accuracy in predicting patient outcomes, generating recommended treatment plans on a patient-specific level, and generating comparisons of various healthcare centers. Gradient boosted regression models may provide improved model performance than traditional regression analysis, particularly with regard to sparse datasets. Using national burn data, the disclosed technology can predict LOS across various healthcare centers while accounting for patient and center-specific characteristics, thereby producing more meaningful O/E ratios. These models provide a risk-adjusted LOS benchmarking using a robust data source for the healthcare centers.

Moreover, the disclosed technology leverages a singular machine learning model to efficiently utilize compute resources and processing power and provide accurate real-time or near real-time patient outcome determinations and care recommendations. The model can be trained with a robust set of data from the plurality of healthcare centers, so that the model can be used in different scenarios to accurately generate patient outcomes, regardless of a type of patient outcome being assessed, other patient information, and/or a particular healthcare center. Deployment of the singular model can advantageously utilize fewer compute resources and processing power than training, identifying, selecting, and/or using multiple models. As a result patient outcome determinations can be accurately and quickly made, especially when requested in real-time or near real-time by a relevant user.

As yet another example, the disclosed technology can generate models effective at creating predictions on small sample sizes. The models can, for example, include a greater number of features than other models. The disclosed models can handle categorical variables natively instead of translating values to numeric values and potentially losing information that could potentially feed into model precision. The modeling techniques described herein can allow for variables included in the disclosed models to be readily, easily, and efficiently refined over time based on input from clinical experts or other relevant users. As an illustrative example, a COVID flag or trauma injury severity can be included as a new feature within the same model over time.

As additional examples, the disclosed technology provides improved precision and accuracy in predicting patient outcomes, improved speeds in processing large sets of data, and increased quantities and types of features and/or variables that can be used in processing the large sets of data and predicting the patient outcomes. These advantages can provide for more robust determinations to be made, especially since large collections of burn patient data from burn centers and other healthcare centers as well as clinical data can be used to train models that predict the patient outcomes. Near-time data collection techniques can also be used to allow for fast turnaround time from admission data (e.g., when a patient is admitted to a healthcare center) to a predicted outcome.

The details of one or more implementations are set forth in the accompanying drawings and the description below. Other features and advantages will be apparent from the description and drawings, and from the claims.

BRIEF DESCRIPTION OF THE DRAWINGS

FIGS. 7A, 7B, and 7C illustrate example variables used with the disclosed techniques and their corresponding importance indicators.

FIGS. 12A, 12B, and 12C illustrate example GUI displays for presenting patient outcomes at a computing device.

FIGS. 15A, 15B, 15C, 15D, 15E, and 15F illustrate example GUIs for viewing patient outcomes and care at a particular healthcare center.

Like reference symbols in the various drawings indicate like elements.

DETAILED DESCRIPTION OF ILLUSTRATIVE EMBODIMENTS

Figure 1:
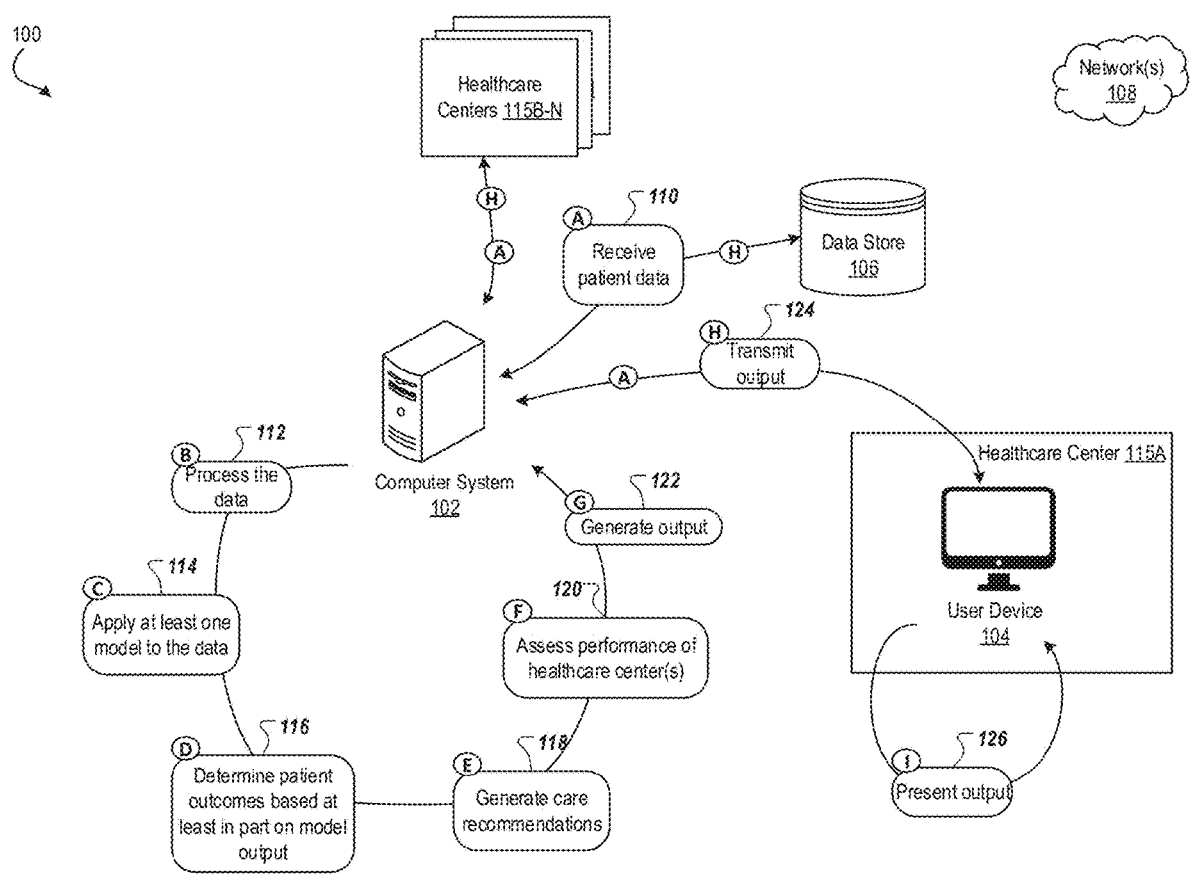
FIG. 1 is a conceptual diagram for determining patient outcomes using machine learning modeling techniques.

This document relates to systems, methods, and computer-modeling techniques for risk-adjusted assessment of different types of patient outcomes at healthcare centers, including but not limited to mortality rates and/or LOS outcomes at burn centers. The disclosed technology can be used to improve quality and delivery of services in individual burn centers and particular patients to reduce or otherwise mitigate predicted mortality rates and/or LOS. As described herein, one or more machine learning models can be implemented to perform the disclosed techniques.

Patient data can be compiled into a dataset for use with the disclosed technology. After a process of data cleansing, de-identification, and/or semantic harmonization by a computer system, one or more machine learning models can be applied to the patient data to determine patient outcomes, generate recommendations for patient-specific treatment plans based on the determined outcomes, and/or generate recommendations for improving healthcare center-wide treatment and care services. An exemplary dataset described throughout this disclosure can include 128,252 records reported by 103 burn centers over a predetermined period of time of 6 years. Datasets having other quantities of records can also be used with the disclosed techniques. Moreover, for inclusion in LOS predictions, a LOS variable can be used with one or more of the disclosed machine learning models. This LOS variable may cause a quantity of records to be excluded for missing LOS data. In the exemplary dataset described herein, 2,123 records can be excluded for missing LOS data. In this exemplary dataset, 23 predictor variables can be selected from over 50 predictor variables, which can all or partially be recorded in the dataset (e.g., based on completeness and/or clinical significance). In some implementations, at least 75% completeness may be required to select the predictor variables. One or more other thresholds can be set to select the predictor variables.

Data analysis can be performed using one or more algorithms, machine learning models, and/or machine learning techniques. For example, gradient boosted regression (e.g., CatBoost), a form of machine learning, can be used to predict mortality or other patient outcomes. This predicted mortality can also be compared to output from a traditional logistic regression model. Comparisons of unpenalized linear regression and gradient boosted regressor models can be performed by measuring $R^2$ and concordance correlation coefficient (CCC) on application of the model to the exemplary dataset. Model performance can be evaluated with area under curve (AUC) and precision-recall (PR) curves. Using the CatBoost predictions, observed to expected (O/E) mortality can be calculated for each healthcare center. Confidence intervals (CI) for O/E analysis in the case of mortality prediction (or other types of patient outcomes) can be calculated using an implementation of a Clopper-Pearson method, such as a normal distribution parameteric model. Analyses can be run on one or more cohorts defined on a patient population in terms of TBSA. For example, a first cohort can contain all patients, the second cohort can contain patients with >=10% but <20% TBSA, and a third cohort can contain patients with >20% TBSA. One or more other cohorts can be determined.

The CatBoost model can achieve, in an illustrative implementation, a test AUC of 0.986 with an average precision of 0.8. The logistic regression, by comparison in the example implementation, can produce an AUC of 0.97 with an average precision of 0.706. In some implementations, the CatBoost model can outperform the linear regression model with a test $R^2$ of 0.68 and CCC of 0.82, compared to the linear regression model having $R^2$ of 0.51 and CCC of 0.69. The CatBoost model may be less biased for higher and lower LOS durations. While accuracy may be near ceiling for both models, the CatBoost model can be more sensitive, which can lead to an improvement in average precision. As a result, the CatBoost models can be used for calculation of O/E ratios.

Gradient boosted regression models can provide improved model precision and sensitivity in comparison to traditional, multivariate, logistic regression models. Accordingly, gradient boosted regression models can be used to predict burn mortality across various burn patients in healthcare centers to determine meaningful O/E ratios. Further, this can allow for comparison of mortality across different centers, regardless of where those centers may be geographically located. Gradient boosted regression models can also provide for predicting LOS outcomes across various healthcare centers for more meaningful O/E ratios. These models can provide a risk-adjusted LOS benchmarking approach that can utilize a robust data source and apply to various different burn care centers.

Referring to the figures, FIG. 1 is a conceptual diagram of a system 100 for determining patient outcomes using machine learning modeling techniques. The system 100 includes a computer system 102, a user device 104, and a data store 106 in communication (e.g., wired, wireless) via network(s) 108. In some implementations, one or more of the components 102, 104, and 106 can be part of a same computing system, network of computing devices, cloud-based computing system, and/or computing device. In other implementations, as shown in FIG. 1, the components 102, 104, and 106 can be separate and/or remote from each other. The disclosed techniques can also be performed remotely and/or in a cloud-based implementation, using cloud-based computing systems and/or networks.

The computer system 102 can receive patient data from the data store 106, the user device 104, and/or computing systems associated with one or more healthcare centers 115A-N (block A, 110). The computer system 102 can also receive other data, including but not limited to healthcare center data associated with any one or more of the healthcare centers 115A-N. Collecting data from a variety of data sources (e.g., healthcare centers 115A-N) in geographically different regions and/or with different practices, care plans, treatment plans can accurately provide for identifying and addressing patterns in patient outcomes that are expected in subpopulations of patients (e.g., burn patients in a particular healthcare center, such as the healthcare center 115A). The data can include, as an illustrative example, burn patient data for patients who suffered and/or have been treated for a burn injury. The received data can be anonymized.

Figure 2:
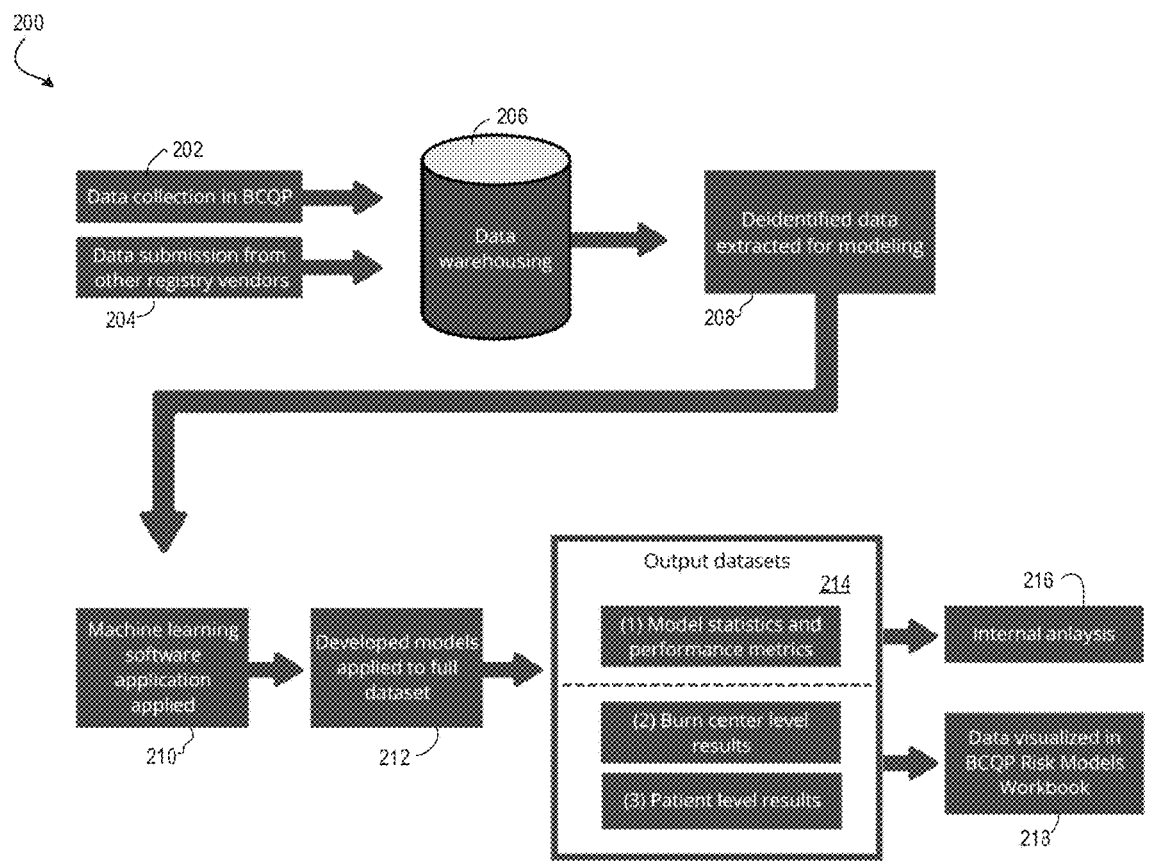
FIG. 2 is a conceptual diagram of a process for processing and harmonizing data for use in the disclosed techniques.

The computer system 102 can process the data (block B, 112), as described in reference to FIG. 2. In some implementations, processing the data can include harmonizing the data and/or anonymizing the data.

The computer system 102 can apply at least one model to the processed data in block C (114). The model can be trained to determine/predict patient outcomes or other types of insights across various different healthcare centers 115A-N.

In block D (116), the computer system 102 can determine patient outcomes based at least in part on model output. In some implementations, the determined patient outcomes can be the output from the model. Various different types of patient outcomes can be determined in block D (116). As an illustrative example, risk and mortality assessments can be performed for burn patients. As another example, LOS outcomes can be performed for burn patients. Patient recovery rates can also be determined for particular patients and based on particular health conditions (e.g., burn, different types of burn conditions, skin conditions, infections, etc.) experienced by such patients.

As an illustrative example, the computer system 102 can receive data about a new patient at the healthcare facility 115A, the data including (for example) diagnosis information, timing of treatment, admission to the center, care/treatment performed after admission, interventions performed on the patient, etc. This data can then be fed into the model as input to determine an expected outcome for the patient, such as their mortality rate and/or expected LOS at the center.

The computer system 102 can also generate one or more care recommendations, specific to a particular patient at one or more of the healthcare centers 115A-N and/or generic/related to practices at the healthcare centers 115A-N (block E, 118). The recommendations can be generated at least in part based on the patient outcomes and/or the model output. The generated recommendations can include best practices that the center as a whole can adopt and/or practice. The recommendations can include best practices and/or treatment plans that the center should follow for the particular patient.

The computer system 102 can assess performance of one or more of the healthcare centers 115A-N based at least in part on the model output, the determined patient outcomes, and/or the generated care recommendations (block F, 120). The computer system 102 can compare the healthcare center 115A to one or more other healthcare centers 115B-N for benchmarking in the industry. Comparing center performance can help each center determine how they can improve their treatment plans and/or overall care provided to patients in their respective center.

In some implementations, blocks D-F (116-120) can be performed simultaneously and/or in any other order after performing block C (114).

The computer system 102 can generate output in block G (122). The output can include GUI displays described throughout this disclosure. The output can also include tables, charts, matrices, and other types of outputs that can be used to visualize information determined using the disclosed techniques.

The computer system 102 can transmit the output to the data store 106 (for storage and later retrieval), the user device 104 at the healthcare center 115A, and/or computing systems/devices at any one or more of the other healthcare centers 115B-N (block H, 124).

The user device 104 can present the output in block I (126) with the GUIs described herein. The output can be used prospectively by a relevant user in the healthcare center 115A, such as a physician, nurse, or other healthcare provider, to provide treatment of a specific, current patient or other current or future patients at the center 115A. Such insights can additionally and/or alternatively be used retrospectively to evaluate and compare performance, treatment, patient outcomes, and/or personnel at different healthcare centers 115A-N. Such evaluations and comparisons can be performed automatically by the computer system 102. In some implementations, such evaluations and comparisons can be performed by the relevant user at the user device 104.

FIG. 2 is a conceptual diagram of a process 200 for processing and harmonizing data for use in the disclosed techniques. The process 200 can be performed by the computer system 102 described herein. One or more blocks in the process 200 can additionally or alternatively be performed by other computing devices, systems, networks, and/or cloud-based systems.

Referring to the process 200, various statistical methods can be used. As an illustrative example, patient data and other healthcare data can be analyzed using PYTHON or similar languages and libraries. A 3-stage data pipeline can be implemented, as shown and described in the process 200 of FIG. 2. In some implementations, missing data may also be imputed. Gradient boosted regression can be selected for a prediction model used with the processed data to determine patient outcomes.

In the process 200, data can be collected, retrieved, and/or received (blocks 202, 204). The data can be collected in a software suite and/or platform provided using the disclosed techniques to relevant users, such as physicians or other healthcare professionals in a healthcare facility. The data can also be provided or submitted by vendors or other external or relevant users (and thus provided to the computer system 102).

The data received in blocks 202 and 204 can be stored using data warehousing techniques in block 206. In some implementations, the data can be received as anonymized data. In some implementations, the data can be anonymized once received and stored in block 206.

De-identified data can be extracted from the data warehousing techniques for modeling in block 208. For example, the data can be split into training and test datasets. Sometimes, the data can be split based on time periods or other temporal aspects. As an illustrative example, the records from 2015-2019 (91% of received data) can be split for the training data and records from 2020 (9% of the received data) can be used as the testing data. This temporal split can beneficially ensure that a trained model can be robust to non-stationarity. One or more other temporal splits or other techniques for splitting the received data can be used in block 208 (e.g., random).

Machine learning software techniques can be applied to the training data in block 210. In other words, the computer system 102 can train the model using the training data.

In some implementations, the computer system 102 can scale continuous variables in the training data and, for the illustrative case of LOS predictions, remove a predetermined quantity of sigma outliers (e.g., 3-sigma outliers). The scaling and outlier limits learned from the training data can subsequently be applied to the test data.

Additionally or alternatively, the computer system 102 can also perform imputation techniques for missed data. PYTHON library techniques can be used to perform the imputation. In some implementations, one or more other iterative imputer techniques can be performed. Imputer performance can be balanced with computational efficiency by choosing Bayesian Ridge Regression for an estimator. For outcome prediction, imputation can be run once. In some implementations, imputation can be run additional times, which can depend on a particular use case and/or data that is being processed. For calculation of observed/expected ratios, the imputation techniques can be sampled 10 times. The imputation techniques can be sampled additional or fewer times based on a particular use case (e.g., type of patient outcomes being determine) and/or the data that is being processed (e.g., type of data, abundance of data, quantity of data).

Imputation technique performance can be validated, in some implementations, by taking a subset of complete records (N=57,317 in an illustrative example) and artificially creating missingness in this subset in proportion to the missingness of the whole dataset, per variable, and training a module that performs the imputation techniques on this dataset. Imputation can substantially increase performance on the real data. In addition to calculating traditional outcome metrics (e.g., accuracy and F1 score for categorical variables, Pearson's r and Spearman's rho for continuous variables), for categorical variables distributional similarity between imputed and actual values can be identified and analyzed. A KLD ratio can be calculated as 1 minus the ratio of the Kullback-Leibler divergence between the imputed and actual distribution to the Kullback-Leibler divergence of the modal value imputation to the actual value. Thus, a positive value may indicate that the imputation performed better than simply imputing the most frequently occurring value.

Additionally or alternatively, bootstrapping can be used for calculated observed/expected (O/E) ratios. As an illustrative example, the dataset can be resampled with N=100 and a proportion of 0.5. Various other resampling quantities and/or proportions can be used. This stage can precede imputation, so each resampled version of the dataset can be imputed separately. As a result, in this illustrative example, 1,000 versions of the model can be trained in blocks 208 and 210.

Once the model is trained, the developed model can be applied to the full dataset in block 212. As a result, the model can be used to determine patient outcomes.

The model can generate output datasets 214 as a result of being applied to the full dataset. For example, the model can generate (1) model statistics and performance metrics, (2) burn center or other healthcare center level results, and/or (3) patient level results. Output such as the (1) model statistics and performance metrics can be fed back to the computer system 102 for internal analysis in block 216. For example, the (1) model statistics and performance metrics can be used to iteratively train and improve the model or other models that are developed and trained in the process 200. One or more of the other output, such as the (2) center level results and/or the (3) patient level results can be visualized in one or more GUIs for presentation to relevant users at their respective user computing devices (block 218).

Figure 3:
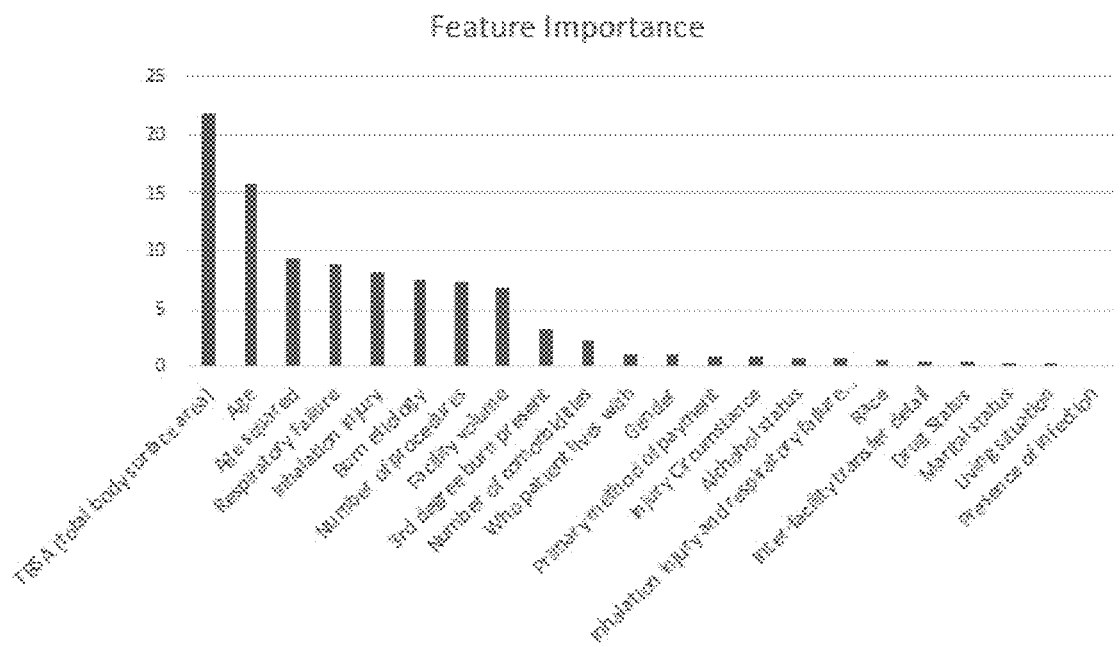
FIG. 3 is a graph indicating feature importance of variables that can be used to determine patient outcomes.

FIG. 3 is a graph 300 indicating feature importance of variables that can be used to determine patient outcomes. Variables closer to a left side of the graph 300 (e.g., closer to the y axis) have a higher feature importance than variables closer to a right side of the graph 300 (e.g., farther from the y axis). The feature importance of each variable can be determined using techniques described herein, such as CatBoost feature selection and other modeling techniques. The determined feature importance of the variables can indicate which variables have a greater effect for model outcomes versus other variables.

Logistic and Linear regressions may often be preferred because of ease with which parameter values can be related to a dependent variable. Similar visibility can be achieved into the influence of predictor variables in a CatBoost model. The CatBoost model can calculate feature importance by measuring the extent to which changing a predictor variable also changes an outcome variable. In some implementations, importance values can be normalized to sum to 100 (or any other predetermined scale and/or numeric or integer range of values). Variables that have traditionally been assigned high importance (e.g., age, TBSA) rank highly in the model, as shown in the graph 300. Other less often employed variables, such as facility volume, also play a significant explanatory role in the model outcomes.

As an illustrative example in the graph 300, focusing on a single feature such as inhalation injury can provide for illustrating feature importance. Inhalation injury in this example may be present in only 6.4% of all records and 7.0% of records in which inhalation injury data was recorded. The difference in outcome between the two groups can be substantial: 17.3 days length of stay for inhalation injury patients versus 7.6 days for non-inhalation-injury patients and consequently the inhalation injury feature can be a $5^{th}$ most important feature. As another example, looking at the feature variable presence of $3^{rd}$-degree burn, this variable had a similar effect on outcome, mean LOS of 15.1 days for patients with $3^{rd}$ degree burn versus 6.1 days for patients without, but a slightly less feature importance, $9^{th}$ of 22. It had a higher prevalence, with 25% of all records reporting it, which also explains its greater importance within the model and as shown in the graph 300.

In some implementations, development of complications may not be used as a predictor with the exception of presence of infection. Number of comorbidities, on the other hand, can be used and may have a relatively high (3.1, $9^{th}$ of 22) feature importance for predicting LOS, higher than both living situation (8, $13^{th}$ of 22) and living companions (8, $13^{th}$ of 22). Overall, the amount of collinearity between variables may be modest. Collinearity between all variable pairs using the absolute value of Pearson's R for continuous variables and Cramer's V statistic for any pair of variables where one was categorical (binning the continuous member of the pair, if there was one, into quintiles in that case) can be calculated. As a result, a high association in a few places as expected was identified, notably between age and age squared (0.95), between inhalation injury and inhalation injury with respiratory failure (0.73) and inhalation injury with respiratory failure and respiratory failure (0.64), and between drug use and alcohol use (0.52). After that, the highest association was between age and number of comorbidities (0.50). The associations between living situation and comorbidities and between living companions and comorbidities were both very modest, 0.11 and 0.28 respectively. Pilot analysis indicated that the addition of age squared to the model can cause a meaningful improvement to model performance.

Figure 4A:
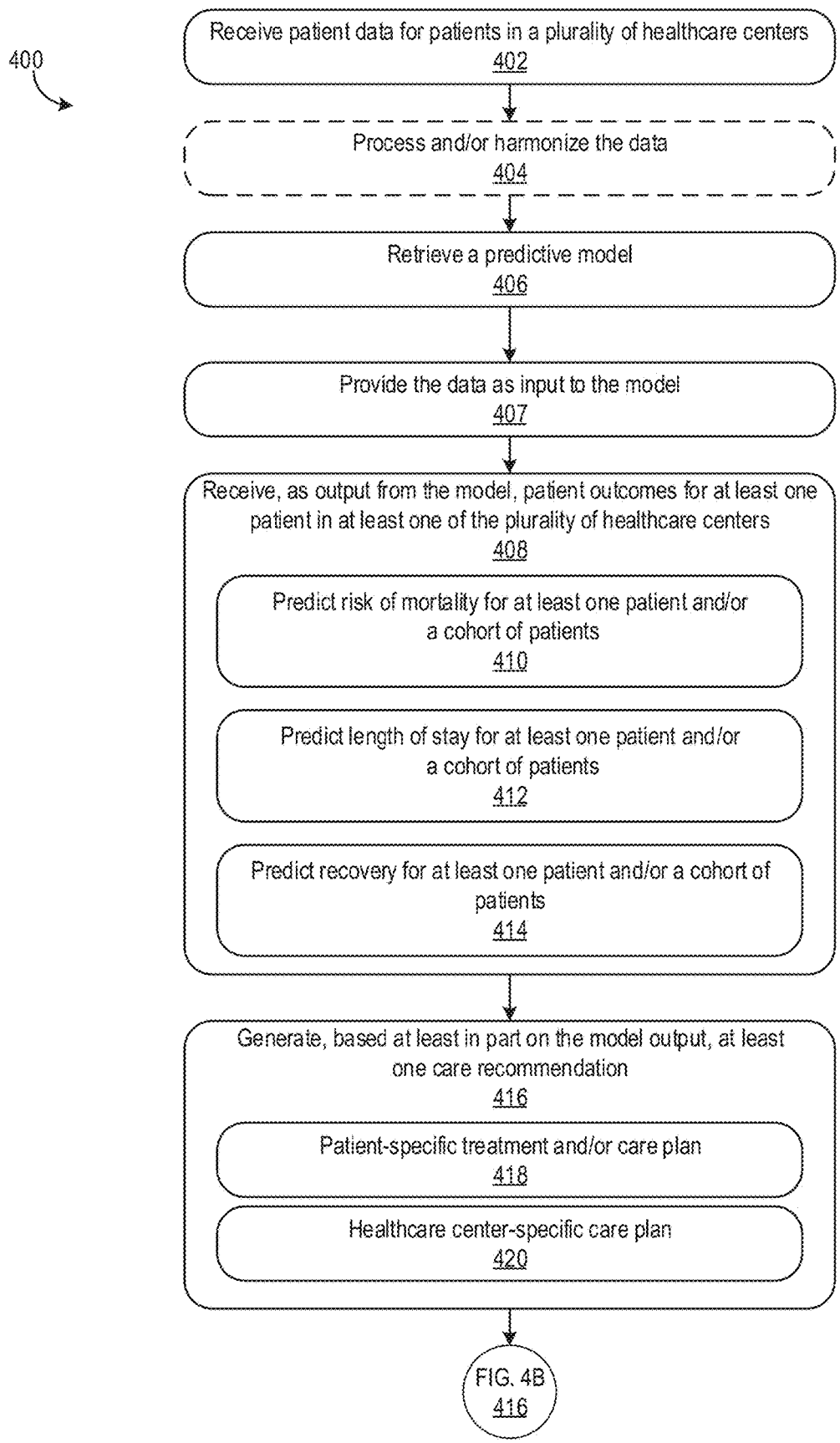
FIGS. 4A and 4B is a flowchart of a process for determining patient outcomes using machine learning modeling techniques.
Figure 4B:
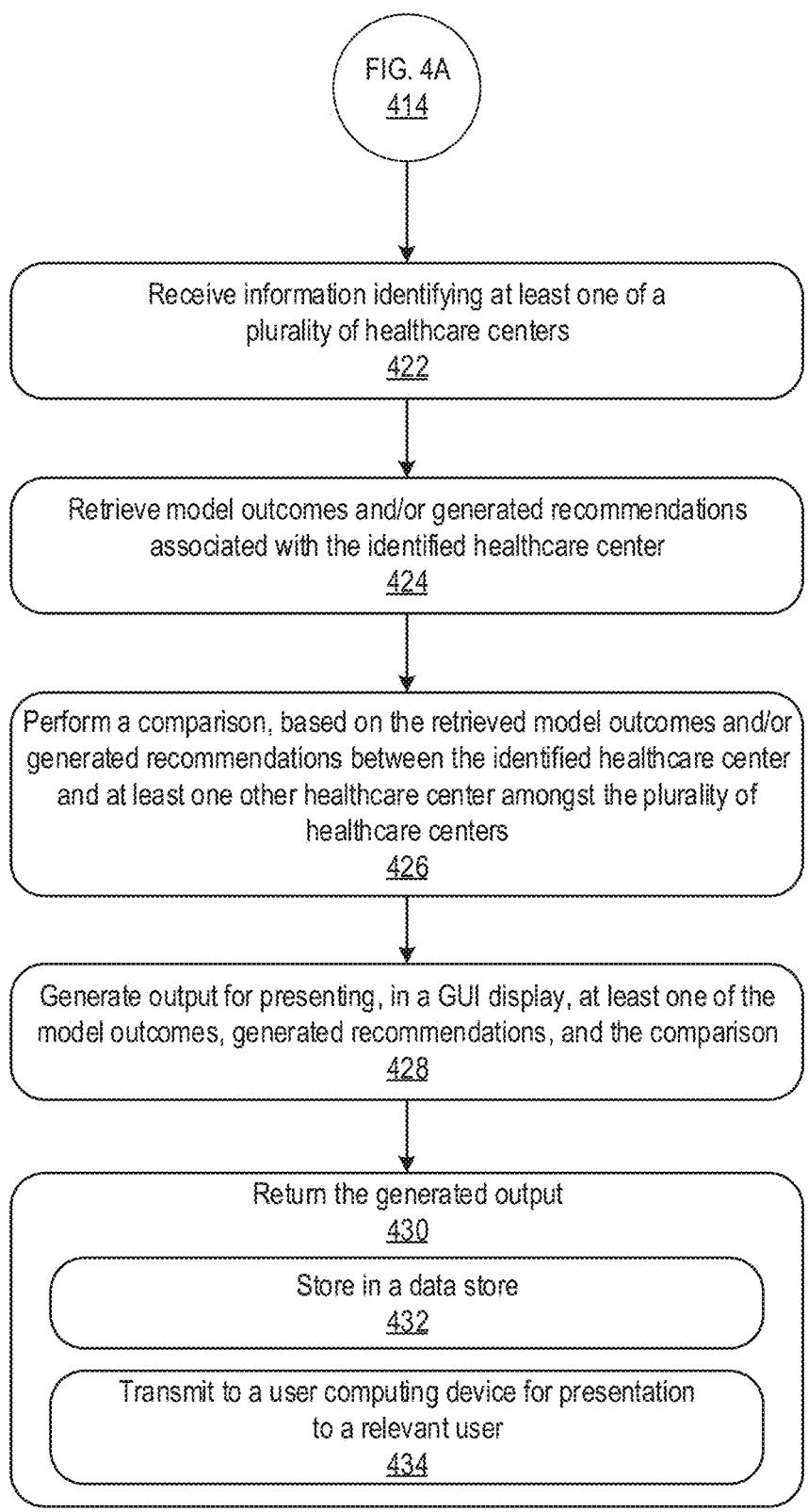

FIGS. 4A and 4B is a flowchart of a process 400 for determining patient outcomes using machine learning modeling techniques. The process 400 can be performed by the computer system 102 described herein. The process 400 can also be performed by any other type of computing system, computing device, and/or cloud-based system described herein. For illustrative purposes, the process 400 is described from the perspective of a computer system.

Referring to the process 400 in FIGS. 4A and 4B, the computer system can receive patient data for patients in a plurality of healthcare centers in block 402. The patient data can be received for healthcare centers that are within a predetermined geographic region. The patient data can also be received for healthcare centers regardless of their geographic region. The patient data can be received for patients experiencing a particular type of condition across the plurality of healthcare centers (e.g., a particular category or type of burn, a particular cause of the burn). The patient data can be received for a predetermined period of time (e.g., a past year, a past 6 months, a past 3 months, a past month). In some implementations, the patient data for all burn patients at all the healthcare centers can be received, which can be advantageous to train a model and use the model during runtime to accurately predict patient outcomes for various different types of patient conditions and/or scenarios, regardless of the healthcare center they are associated with. In some implementations, the computer system can receive patient data for a particular healthcare center rather than the plurality of healthcare centers. The data can include, but is not limited to, patient demographics, place of occurrence, burn etiology, burn size (percent of total body surface area affected by burns (% TBSA)), patient weight, volume of fluid administered by fluid type and hospitalization time period, discharge status, and/or other clinical and treatment measures.

Sometimes, the computer system can continuously receive the patient data from computing systems at the plurality of healthcare centers. The computer system can also transmit a request for the patient data to the computing systems at the plurality of healthcare centers at predetermined time intervals (e.g., every 1 day, every week, every 2 weeks). In some implementations, the patient data can be stored in one or more data stores and the computer system can access the data store(s) to retrieve the patient data in block 402. The computer system may also receive the patient data from the computing systems at the plurality of healthcare centers and/or retrieve the patient data from the data store(s) in response to receiving a request from a user computing device to perform an analysis of patient treatment at one or more healthcare centers. For example, using the disclosed GUIs, a relevant user can request to view predicted mortality rates for burn patients in a particular geographic region. The user request can be provided as input at the user computing device, then transmitted to the computer system. The computer system can then perform the process 400 in response to receiving the user input.

In block 404, the computer system can optionally process and/or harmonize the data. Refer to FIG. 2 for further discussion.

The computer system can retrieve a predictive model in block 406. The model can be retrieved from a data store described herein. In some implementations, the model may be locally stored and accessible at the computer system. The model can be trained using the techniques described further below. The model can be, for example, a gradient boosted regression model, such as a CatBoost model. The model can be trained with patient data from a plurality of healthcare centers to predict various different types of patient outcomes. In some implementations, the model can also be trained to generate care recommendations for patients and/or a healthcare center as a whole. Since the model can be trained with a robust set of data from the plurality of healthcare centers, a singular model can be used in different scenarios to accurately generate patient outcomes, regardless of a type of patient outcome being assessed, other patient information, and/or a particular healthcare center. Deployment of the singular model can advantageously utilize fewer compute resources and processing power than training, identifying, selecting, and/or using multiple models. As a result patient outcome determinations can be accurately and quickly made, especially when requested in real-time or near real-time by a relevant user.

The computer system provides the data as input to the predictive model in block 407.

The computer system may then receive, as output from the model, patient outcomes for at least one patient in at least one of the plurality of healthcare centers (block 408). For example, using the model, the computer system can predict a risk of mortality for at least one patient and/or a cohort of patients (block 410). As another example, using the model, the computer system can predict a length of stay (LOS) for at least one patient and/or cohort of patients (block 412). As yet another example, using the model, the computer system can predict a recovery (e.g., length of time to full or near-full recovery, type of recovery, expected recovery) for at least one patient and/or a cohort of patients (block 414). Then, at least one patient and/or cohort of patients can be determined by a relevant user and provided as user input at their respective user computing device, then transmitted to the computer system. The at least one patient and/or cohort of patients can also be predetermined by the computer system or a relevant user.

The predicted patient outcomes can also include any other type of outcome for burn patients as well as other types of patients or patients having other conditions. For example, the computer system can predict time to first wound excision, taking into account factors including but not limited to admission source and time from injury to admission. As another example, the computer system can predict percent wound closure at time of discharge given a combination of underlying patient, injury, and/or care pathway data points (or other relevant data points). A prediction of time to wound closure can be helpful in expectation setting with a patient and the patient's caregivers as well as the healthcare center staff to support resource planning. As yet another example, the computer system can predict unplanned readmissions after patient discharge, which can be helpful for post-acute care management approach. Patients with higher likelihood for an unplanned readmission can be engaged more frequently in different ways than patients with a lower predicted probability of unplanned readmission. Another example includes the computer system predicting probability to experience one or more of the following complications, which can influence care pathways that a particular patient is managed under: Compartment Syndrome, Deep Venous Thrombosis, Hospital Acquired Pressure Induced Skin and Soft Tissue Injury, Severe Sepsis, and Superficial Incisional Surgical Site Infection. One or more other patient outcomes can also be predicted using the disclosed techniques described herein.

In block 416, the computer system may generate, based at least in part on the model output, at least one care recommendation. In some implementations, the care recommendation can be generated by the predictive model. In yet some implementations, the computer system can provide the model output from block 408 as input to another machine learning trained model. The another model can be trained to generate the at least one care recommendation based on the model output.

The at least one care recommendation can include a patient-specific treatment and/or care plan (block 418). For example, the care recommendation(s) can indicate a particular type of ointment and application instructions for a particular patient, which can be at least in part based on analysis of patient data for other patients indicating that those patients experienced improved recovery by using that ointment and application. As another example, the care recommendation(s) can indicate how long the particular patient should remain at the healthcare center, which can also be based on the analysis of the patient data for the other patients indicating their length of stays relative their recovery rates.

The at least one care recommendation can include a healthcare center-specific care plan (block 420). For example, the computer system can compare generate care plans and/or practices at a particular healthcare center to a subset of the plurality of healthcare centers to identify ways in which the particular healthcare center can improve its care plans and/or practices. The computer system can then generate the recommendation(s) based on such a comparison. The recommendations can include, as merely illustrative examples, having more healthcare personnel on staff to provide more patient support and/or interaction, having more frequent daily or other temporal checkups on patients under their care, etc.

The algorithms described herein can also be trained to optimize products used in care delivery during different stages of wound healing. For example, the computer system can utilize a model or algorithm that can be trained to determine appropriate fluids to use to limit burn conversion, dermal substitutes to temporize burns, diagnostic tools to aid in the debridement and excision of a burn wound, dermal substitutes to reduct donor site morbidity and autografting, and/or other wound healing product to accelerate healing and reduce probability of negative patient outcomes.

The computer system can receive information identifying at least one of a plurality of healthcare centers (block 422). The information can be received as user input that is provided by the relevant user at their respective user computing device. For example, using one or more of the GUIs described further below, the user can request to view information about how a particular healthcare center performs relative a population of healthcare centers. This request can be provided as user input and transmitted to the computer system in block 422. The request can include information that identifies the particular healthcare center of interest in addition to, for example, particular metrics that the user desires for the comparison. As an illustrative example, the user can request viewing performance of the particular healthcare center amongst the population of healthcare centers for burn patients that are females between ages 13-29.

The computer system can retrieve model outcomes and/or generated recommendations associated with the identified healthcare center (block 424). The model outcomes and/or recommendations can be retrieved from a data store described herein (e.g., when the outcomes and/or recommendations are determined at an earlier time than at least block 422). In some implementations, this information can be locally stored at the computer system, especially if the outcomes and recommendations are performed within a same or similar period of time as receiving the healthcare center information in block 422.

In block 426, the computer system can perform a comparison, based on the retrieved model outcomes and/or generated recommendations between the identified healthcare center and at least one other healthcare center amongst the plurality of healthcare centers. The computer system can retrieve the model outcomes and/or recommendations for the at least one other healthcare center (which can occur in block 424, in some implementations) to then be compared with the outcomes and recommendations of the identified healthcare center. The computer system may also create one or more reports that allow relevant users to quickly and easily understand if their performance for a particular patient cohort is statistically significantly better or worse than their peers. For example, the reports can show relevant user performance per cohort via a color coding of their respective data. The computer system may also provide insights into overarching trends in burn care and accurately put an individual burn center or other healthcare center's performance in the context of year over year national changes. By visualizing the trend of a particular center's results over time, the center can readily see and quantify an impact of their own quality improvement activities. For example, a burn center may introduce a new quality improvement position and can see a change in patient outcomes and care before and after that time point.

As an example, the computer system can identify that the identified healthcare center has a higher rate of mortality amongst female patients between ages 50-69 than more than 50% of the plurality of healthcare centers. As a result, the computer system can determine that the identified healthcare center can improve its care and treatment services in order to reduce its rate of mortality and perform more similarly to the other plurality of healthcare centers. As another example, the computer system can identify that on average the identified healthcare center has a lower LOS than most other of the plurality of healthcare centers. As a result, the computer system can determine that the identified healthcare center has sufficient or improved care services compared to the other healthcare centers. Various other comparisons may be made to benchmark the identified healthcare center amongst the plurality of healthcare centers.

In some implementations, an outcome variable of interest can include fluid therapy type (e.g., crystalloids, colloids, and blood products) and volume (mL) administered during a first 24 hours and subsequent 24 to 48 hours of in-hospital treatment (or other predetermined amount of time, which can be determined or specific to a particular healthcare center and/or patient condition). Crystalloids can include Lactated Ringer's (LR), Hartman's solution, etc. Colloids may include albumin (all concentrations), hydroxyethyl starch (all concentrations), other starch fluids, and/or non-blood product colloids. Blood products can include whole blood (WB), packed red blood cells (PRBCs), platelets, fresh frozen plasma (FFP), cryoprecipitate, and/or others that may be reported by the healthcare centers.

Patient characteristics variables may also be used to predict patient outcomes. These variables can include, but are not limited to, patient age (at time of admission), patient weight, % TBSA, burn etiology (e.g., flame, flash, scald, electrical, rash/skin infection, friction/shearing, contact, chemical/corrosion, radiant/laser burn/cold injury, inhalation injury only, and not known/not recorded), and/or admission source (e.g., transfer from an emergency department or ambulatory care center, direct from scene of injury, transfer from another acute care facility, admissions from burn center outpatient office/clinic, and not known/not recorded).

In some implementations, descriptive statistics for fluid type and/or volume may also be computed by healthcare center to assess variability in treatment across the centers. Various other factors, features, and/or variables can be used as described herein to perform the disclosed techniques.

Descriptive statistics (e.g., frequencies and percentages for categorical variables; means, medians, and standard deviations for continuous variables) can be computed for variables used to assess and compare healthcare centers. Normalized fluid volumes can be calculated, for example, using the formula: Normalized fluid volume=ml/kg/% TBSA, where ml can be volume of fluid delivered to a patient during a stated timeframe, kg can be the patient's weight on admission, and % TBSA can be a percent of total body surface area affected by burns. As an illustrative example of comparing healthcare centers, a total of 7,359 patient burn cases can be received. Of those cases, 614 (8%) cases may have a percentage of TBSA affected by burns of 20% or more. Of those 614 cases, 418 (68%) cases can have associated fluid values. Of those 418 cases, 398 cases (95%) can have fluid values during a 0 to 24-hour period after admission. Table 1 below shows descriptive statistics for age and TBSA % for the 614 cases with a TBSA≥20% without regard to fluid treatment and for the 398 cases with a TBSA≥20% who received any fluid during the first 24 hours after admission. The mean and median TBSA % values appear similar for the two groups; however, the group with any fluid values 0 to 24 hours after admission is slightly older. Also, slightly over 20% of patients in both groups had missing values for age.

TABLE 1

Descriptive Statistics for Age and TBSA by Fluid Timing

| | Cases with TBSA ≥20% N = 614 | | | | Cases with TBSA ≥20% and any Fluid Values 0-24 Hours after Admission N = 398 | | | |
|---|---|---|---|---|---|---|---|---|
| Variable | % Missing | Median | Mean | SD | % Missing | Median | Mean | SD |
| Age (yrs) | 20.5% | 38 | 38.0 | 23.3 | 21.6% | 43 | 41.5 | 22.1 |
| TBSA % | 0% | 31 | 36.4 | 21.8 | 0% | 33.5 | 37.7 | 21.0 |

Frequencies and percentages of cases by burn etiology are presented in Table 2 below. The percentages are similar between the group with TBSA≥20% without regard to fluid treatment and the group with TBSA≥20% that received any fluid 0 to 24 hours after admission regarding burn etiology with flame, flash, and scald as the three most frequent etiologies accounting for approximately 90% of cases in both groups.

TABLE 2

Frequencies and Percentages by Burn Etiology and Fluid Timing

| | Cases with TBSA ≥ 20% N = 614 | | Cases with TBSA ≥ 20% and any Fluid Values 0-24 Hours after Admission N = 398 | |
|---|---|---|---|---|
| Burn Etiology | N | % | N | % |
| Flame | 390 | 63.5 | 265 | 66.6 |
| Flash | 78 | 12.7 | 64 | 16.1 |
| Scald | 77 | 12.5 | 37 | 9.3 |
| Electrical | 20 | 3.3 | 9 | 2.3 |
| Rash/Skin Infection | 19 | 3.1 | 5 | 1.3 |
| Not known/Not recorded | 10 | 1.6 | 5 | 1.3 |
| Friction/Shearing | 6 | 1.0 | 4 | 1.0 |
| Contact | 5 | 0.8 | 4 | 1.0 |
| Chemical/Corrosion | 4 | 0.7 | 3 | 0.8 |
| Radiant/Laser Burn/Cold Injury | 4 | 0.7 | 2 | 0.5 |
| Inhalation Injury Only | 1 | 0.2 | 0 | 0.0 |
| Total | 614 | 100.1[a] | 398 | 100.2[a] |

[a]Does not sum to 100.0% due to rounding.

Table 3 shows the frequencies and percentages of cases by admission source. The group with TBSA≥20% that received any fluid 0 to 24 hours after admission had a slightly higher percentages of cases admitted by transfer from an emergency department or ambulatory care center and direct from scene of injury and a slightly lower percentage of cases admitted by transfer from another acute care facility compared to the group with TBSA≥20% without regard to fluid treatment. In both groups, over 80% of cases were admitted by transfer from an emergency department or ambulatory care center or direct from scene of injury.

TABLE 3

Frequencies and Percentages by Admission Source and Fluid Timing

| Admission Source | Cases with TBSA ≥ 20% N = 614 | | Cases with TBSA ≥ 20% and any Fluid Values 0-24 Hours after Admission N = 398 | |
|---|---|---|---|---|
| | N | % | N | % |
| Transfer from an Emergency Department or Ambulatory Care Center | 267 | 43.5 | 198 | 49.7 |
| Direct from Scene of Injury | 241 | 39.3 | 164 | 41.2 |
| Transfer from Another Acute Care Facility | 99 | 16.1 | 34 | 8.5 |
| Admissions from Burn Center Outpatient Office/Clinic | 5 | 0.8 | 1 | 0.3 |
| Not known/Not recorded | 2 | 0.3 | 1 | 0.3 |
| Total | 614 | 100.0 | 398 | 100.0 |

Table 4 shows descriptive statistics for fluid volume delivered to patients with a TBSA≥20% who received fluids within the first 24 hours and the subsequent 24 to 48 hours after the injury in both the pre-hospital and in-hospital phases. As expected, crystalloids were used in more patients and with higher volumes, followed by colloids and FFP in all groups.

TABLE 4

Fluid Volume for All Patients with TBSA ≥20% by Hospital Status and Fluid Timing

| | Grand Total | | Fluid Location/Fluid Timing | | | | | | | |
|---|---|---|---|---|---|---|---|---|---|---|
| | | | Pre-hospital | | | | In-hospital | | | |
| | | | Initial 24 hours | | Subsequent 24-48 hours | | Initial 24 hours | | Subsequent 24-48 hours | |
| Fluid Type | Cases with Fluid Values | Avg Fluid Vol (ml) | Cases with Fluid Values | Avg Fluid Vol (ml) | Cases with Fluid Values | Avg Fluid Vol (ml) | Cases with Fluid Values | Avg Fluid Vol (ml) | Cases with Fluid Values | Avg Fluid Vol (ml) |
| Crystalloid | 416 | 6416 | 263 | 2449 | 14 | 2627 | 401 | 9212 | 320 | 6340 |
| Colloid | 236 | 1646 | 38 | 132 | 9 | 0 | 204 | 2428 | 155 | 1083 |
| Blood Products | | | | | | | | | | |
| PRBC | 94 | 210 | 34 | 150 | 8 | 0 | 81 | 267 | 63 | 196 |
| FFP | 141 | 810 | 35 | 93 | 8 | 0 | 130 | 1095 | 77 | 738 |
| Cryo | 63 | 13 | 32 | 16 | 8 | 0 | 59 | 15 | 52 | 12 |
| WB | 64 | 10 | 32 | 8 | 8 | 0 | 59 | 17 | 52 | 5 |
| Platelets | 71 | 25 | 31 | 0 | 8 | 0 | 63 | 36 | 56 | 31 |
| Other | 63 | 168 | 29 | 0 | 8 | 0 | 58 | 227 | 46 | 227 |
| Grand Total | 418 | 3009 | 267 | 1332 | 18 | 518 | 404 | 4143 | 321 | 2776 |

Still referring to the process 400 in FIGS. 4A and 4B, in block 428, the computer system can generate output for presenting, in a GUI display, at least one of the model outcomes, generated recommendations, and/or the comparison.

The computer system can return the generated output in block 430. For example, the computer system can store the output in a data store in block 432. As another example, the computer system can transmit the output to a user computing device for presentation to the relevant user in block 434. Refer to the GUIs described throughout this disclosure for further discussion about the output, such as in FIGS. 6A, 6B, 6C, 6D, 6E, 12A, 12B, and 12C.

In some implementations, the process 400 can stop after block 420. The remaining blocks 422-434 can be performed at another time and/or in another/separate process. For example, the blocks 422-434 can be performed at a later time in response to a relevant user requesting information in a GUI display about performance of one or more healthcare centers, care and treatment plans offered by the healthcare center(s), and/or patient-specific care or treatment information. The patient outcomes and/or care recommendations in blocks 400-420 can be determined at an earlier time and stored in a data store. As a result, when the user requests the information as mentioned above, the computer system can retrieve the predetermined patient outcomes and/or care recommendations from the data store and provide the retrieved information to the user's computing device for presentation in one or more of the GUIs described throughout this disclosure.

Figure 5:
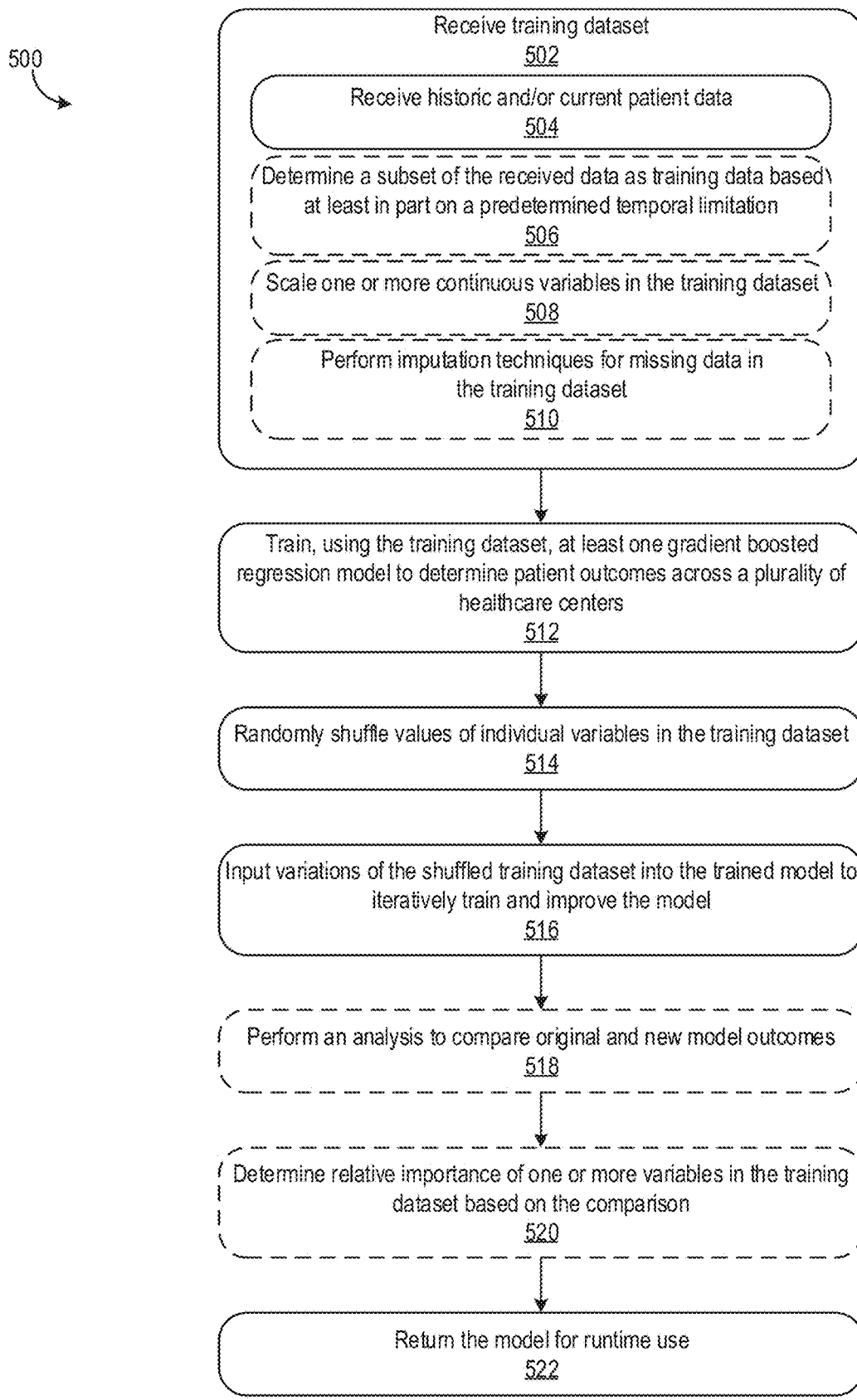
FIG. 5 is a flowchart of a process for iteratively training and improving a machine learning model that is used with the disclosed techniques.

FIG. 5 is a flowchart of a process 500 for iteratively training and improving a machine learning model that is used with the disclosed techniques. The process 500 can be performed by the computer system 102 described herein. The process 500 can also be performed by any other type of computing system, computing device, and/or cloud-based system described herein. For illustrative purposes, the process 500 is described from the perspective of a computer system.

Referring to the process 500 in FIG. 5, the computer system can receive a training dataset in block 502. As part of receiving the training dataset, the computer system may receive historic and/or current patient data (block 504). Refer to block 402 in the process 400 of FIGS. 4A and 4B for further discussion about receiving the patient data and the patient data that can be received.

The computer system may optionally determine a subset of the received data as training data based at least in part on a predetermined temporal limitation (block 506). For example, the computer system may identify all patient data having a date/timestamp between the years 2020-2023 as the subset of data to be used for training. The temporal limitation can also be any other predetermined period of time, including but not limited to a past month, couple months, year, multiple years, etc. The computer system can, in some implementations, determine the subset for training based on other predetermined conditions and/or factors, such as a type of patient condition, type of patient outcome, geographic region of healthcare centers linked to the patient data, patient demographics, etc.

The computer system can also optionally scale one or more continuous variables in the training dataset in block 508. Refer to discussion in FIG. 2 for additional details.

In block 510, the computer system may optionally perform imputation techniques for missing data in the training dataset. The imputation techniques can beneficially provide for making a more robust dataset for training purposes so that a model trained with the training dataset can accurately predict various different patient outcomes regardless of patient data that is received as input to the model during runtime. Refer to discussion in FIG. 2 for additional details about the imputation techniques In block 512, the computer system can train, using the training dataset, at least one gradient boosted regression model to determine patient outcomes across a plurality of healthcare centers. As described herein, the computer system can train a singular model, which provides various benefits and advantages in efficient use of compute resources and processing power. The model can be a CatBoost model, in which many parameters may be combined in a complex way to generate input from output, where it may not be immediately clear how to relate inputs to outputs. The CatBoost model does generate feature importances which can reflect to which change in input determines a change in output. Sometimes, these feature importances can be abstract, sum to 100 by design, and therefore serve to demonstrate relative importance of features to each other.

In some implementations a perturbation analysis can be performed for the trained model. For example, the computer system can randomly shuffle values of individual variables in the training dataset in block 514. The computer system can then input variations of the shuffled training dataset into the trained model to iteratively train and improve the model (block 516). Blocks 514 and 516 can be performed to assess first-order effects, that is, in each dataset variation, only one variable at a time may be shuffled. The effect of this perturbation can then be assessed on the model predictions, by calculating a standard deviation of residuals between original and new predictions made by the model. For continuous variables, dividing this value by the standard deviation of the shuffled variable can provide for approximating dependency between that variable and outcome, in the appropriate units. Thus, the computer system can optionally perform an analysis to compare the original and new model outcomes in block 518. The computer system may also optionally determine relative importance of one or more variables in the training dataset based on the comparison in block 520. Once the relative importance is determined, the results can be reviewed with key experts to assess an impact to model explainability. Additionally or alternatively, the selected features can trigger activities within data providers to enhance completeness and accuracy of data elements. The model can also point out notable features for a specific patient case to aid a clinician or other relevant user in interpretation and determining subsequent action to take for the particular patient.

The model can then be returned for runtime use in block 522. Returning the model can include storing the model in a data store for later retrieval and use. Returning the model can include locally storing the model for real-time or near real-time use in determining patient outcomes.

In some illustrative examples, the computer system can perform a zero analysis to cover potential scenarios, such as respiratory failure, that may fail to impact model predictions as measured by perturbation analysis. After all, perturbation analysis may be applied at a population level and a scenario such as respiratory failure may be very rare and/or unlikely across the population level (moreover, this scenario could be applicable to all categorical variables if the variables are one-hot encoded). For the zero analysis, patient data indicating that the respiratory failure occurred can be subselected, and a variable in question can be zeroed out. Then, the new model predictions can be compared to the old model predictions. The root mean square error, for regression, or change in accuracy, for classification, can measure an impact of this variable on outcome, again expressible in outcome units (e.g., days, mortality probability).

In yet some implementations, LIME, DALEX, and/or Shapley values can be applied to a classification model, which can sometimes be implemented within CatBoost. These training techniques described in the process 500 can be used to explicate contribution of individual variables to model output at the population level and/or the patient level. In some implementations, extend perturbation and zero analyses can be extended to patient-level predictions to determine which patient data points may be driving the predictions in a particular patient's case.

For example, Shapely values can be defined over a dataset or population and pertain (in a healthcare context), to a difference between an individual patient's outcome and a mean outcome across patients. In particular, for each patient record and outcome, Shapley values can be used to decompose that difference into a simple sum of factors associated with each feature of the model. Advantageously, Shapley values for tree-based models, such as CatBoost models, can reduce computation time. As an illustrative example, calculation of Shapley values for dozens of variables and ~130,000 records of patient data may utilize less than 10 seconds of processing time on a single low-cost computing system. Furthermore, some CatBoost models have built-in Shapley value calculations, which can require less custom coding than other models. As a result, the disclosed techniques can be easily and quickly implemented.

FIGS. 6A, 6B, 6C, 6D, and 6E illustrate example graphical user interface (GUI) for presenting patient outcomes and other analysis based on patient data at a computing device. The GUIs described herein can be presented in GUI displays at user devices, such as the user device 104 in FIG. 1.

Figure 6A:
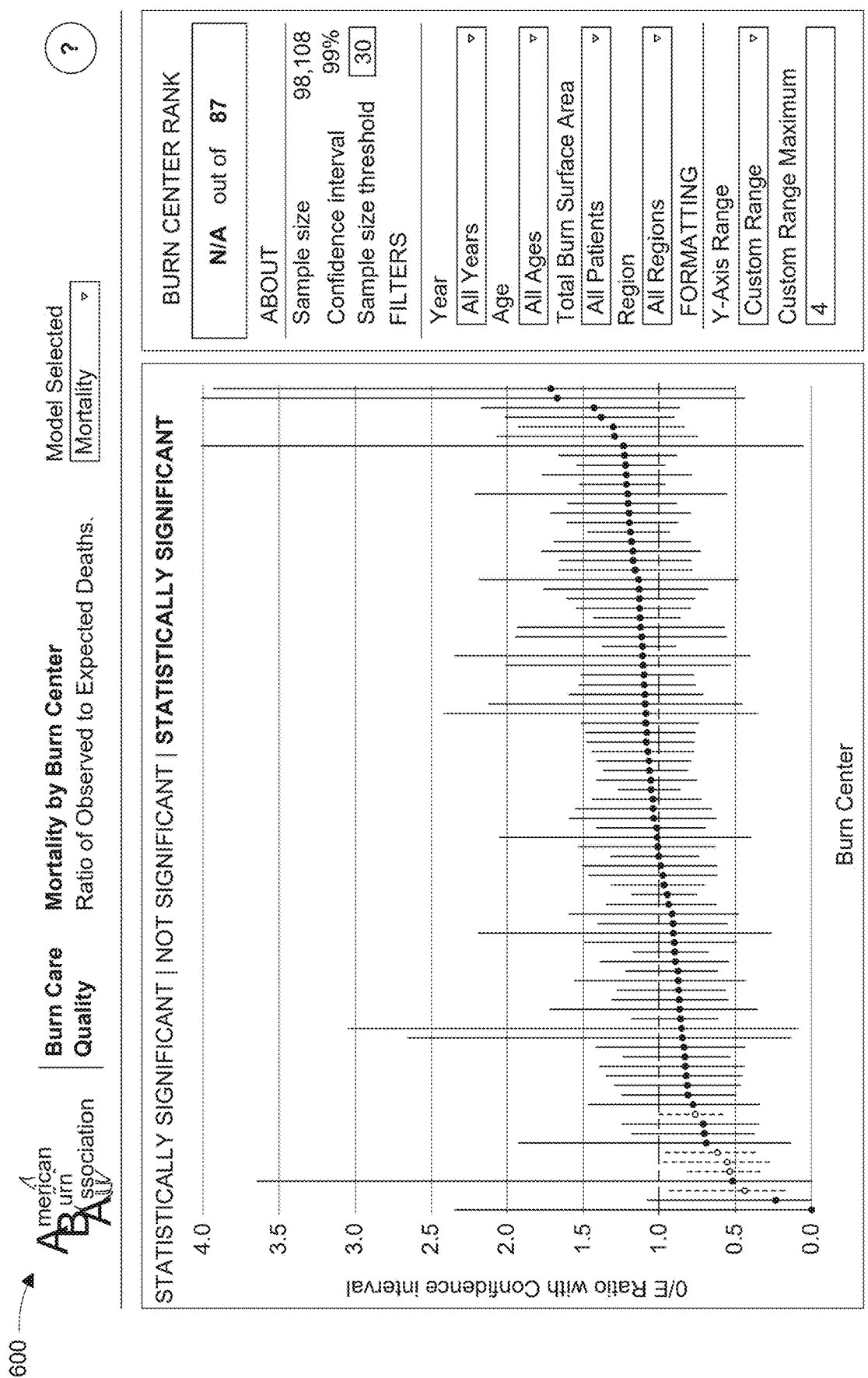
FIGS. 6A, 6B, 6C, 6D, and 6E illustrate example graphical user interface (GUI) displays for presenting patient outcomes at a computing device.

FIG. 6A is an example GUI 600 for presenting information about burn centers performance based on a mortality metric. The GUI 600 can illustrate a graph, plot, or other visual displaying mortality by healthcare center as a ratio of observed to expected deaths. Using the GUI 600, the user can view where any particular healthcare center falls on a continuum of healthcare centers as it relates to risk-adjusted outcomes. Data from in-patient admissions from various centers can be harmonized and standardized to maximize longitudinal analytic value, as shown in the GUI 600.

Figure 6B:
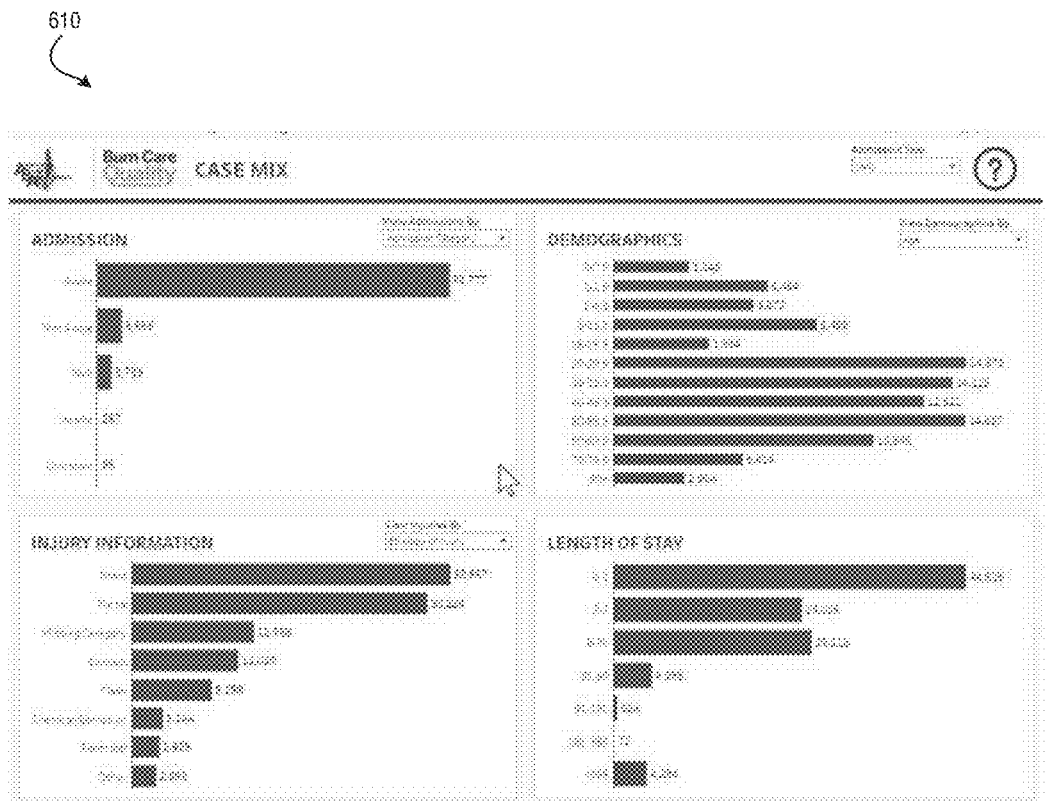

FIG. 6B is an example dashboard GUI 610 for displaying patient cases according to different variables. In the GUI 610, cases are shown according to the following variables: admission to healthcare centers, demographics (e.g., age), injury information, and length of stay in the healthcare centers. The GUI 610 can also present cases corresponding to a variety of other variables described herein. In some implementations, a relevant user can identify and select which variables they would like to view cases by. The GUI 610 can then be updated to present the patient cases based on the user input. Although the cases are shown in the GUI 610 as bar graphs, various other visualizations can be used as depicted and described herein.

One or more particular variables can be key factors that drive modeling of patient outcomes and/or cases. For example, these variables can include, but are not limited to, area affected, inhalation injury, type of burn, chemical, flame, and/or flash burn. Risk adjusted modeling can be used as described herein to determine/predict patient outcomes, which are then presented in the GUI 610 as shown and described herein. The relevant user can also provide user input to update the GUI 610 to visually present patient outcomes (e.g., mortality, scarring, length of stay, outcomes beyond mortality, ability to return to work, time to return to work, etc.) for particular patient cohorts and/or different healthcare center cohorts.

Figure 6C:
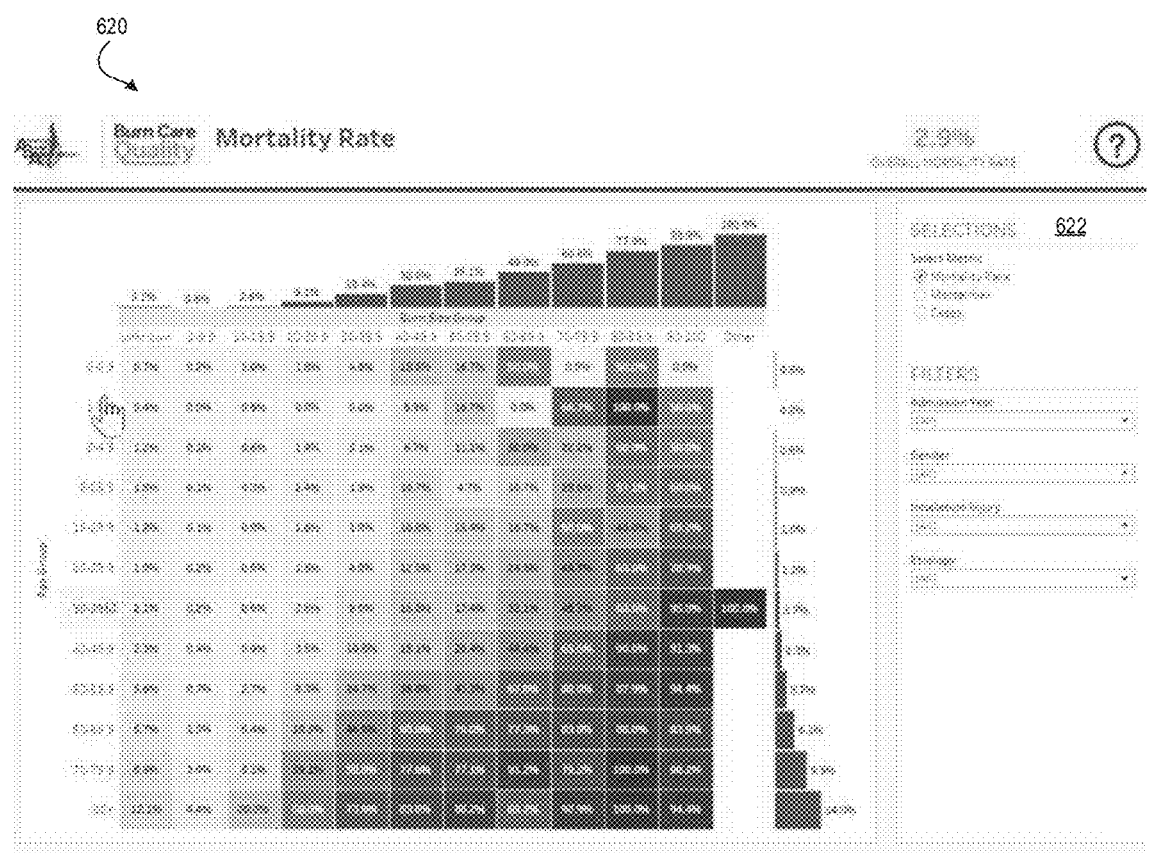

FIG. 6C is an example GUI 620 for presenting mortality rates based on age. The GUI 620 can provide a visual indication of an overall mortality rate for a particular healthcare facility and/or across a group of healthcare facilities according to age. The GUI 620 presents the mortality rates based on age in a shaded matrix, where darker shading indicates higher percentage of mortality rate for a particular age and lighter shading indicates lower percentage of mortality rate for the particular age. The GUI 620 can also present a filtering section 622, which the relevant user can use to adjust how mortality rates are depicted in the GUI 620. For example, the user can provide user input to adjust how mortality rates are visualized as increasing or decreasing for each age group (or a particular age group). The user can also provide user input to adjust how mortality rate is depicted with regards to type of burn (e.g., etiology such as full body burn or scald from coffee), and/or inhalation history (e.g., whether inhaled smoke as well or now). Other filters may also be available in the filtering section 622, including but not limited to gender and other demographics.

Figure 6D:
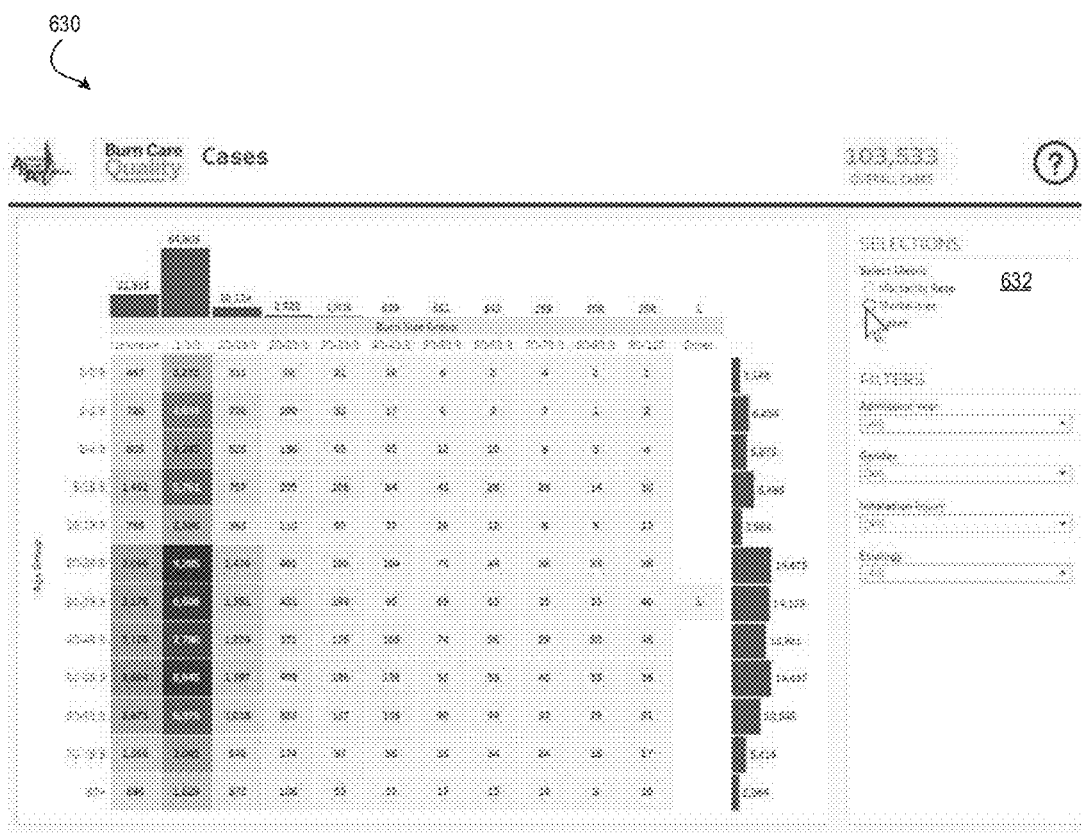

FIG. 6D illustrates a GUI 630 for viewing quantity of cases per age group for use in predicting and modeling patient outcomes. The GUI 630 can present similar information as depicted and describe in reference to the GUI 620 in FIG. 6C. The GUI 630 can also include a filtering section 632 where the relevant user can provide input for adjusting how case information is displayed in the GUI 630. In some implementations, a particular healthcare center can view their cases and/or patient outcomes in comparison to other healthcare centers, across different patient cohorts, and/or across different healthcare center cohorts (e.g., those in region, other pediatric burn centers, etc.). The filtering section 632 can also be used by the user to provide input indicating different characteristics and/or variables to compare a particular healthcare center with one or more other healthcare centers, including but not limited to pediatric/adult, types of fluids delivered to patients, number of patients, etc.

Figure 6E:
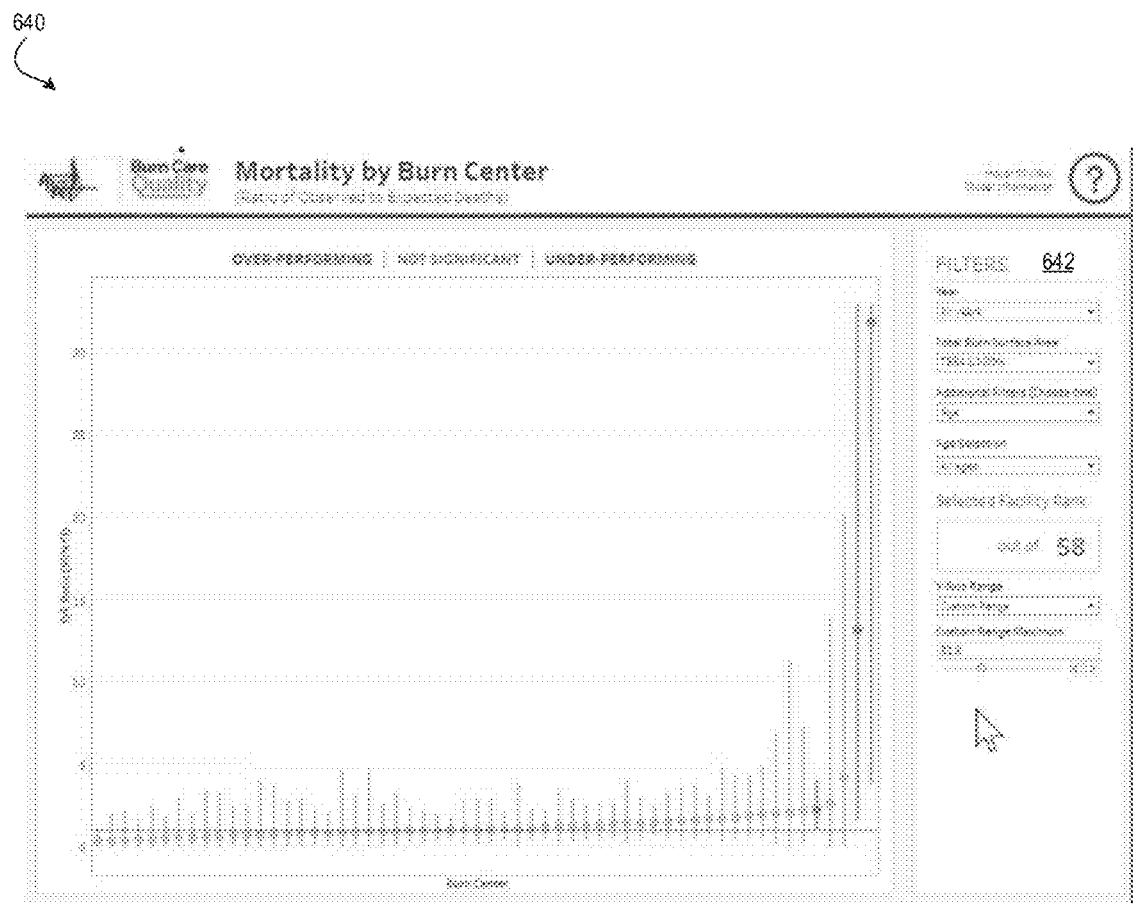

FIG. 6E illustrates a GUI 640, which presents mortality as a patient outcome by burn center as a ratio of observed to expected deaths. The GUI 640, like the other GUIs described herein, can be utilized by the relevant user to identify reasons why some healthcare centers may outperform others. One or more survey tools can be built into a software suite or application containing at least the GUI 640 that allows healthcare centers to ask and answer questions about their treatment plans and/or overall care services. Data collected from the survey can then be synthesized (e.g., harmonized, processed) and then outputted, such as in a graph like that in the GUI 640, to indicate, to a particular center, how other centers operate and what the particular center can do to improve their care like the other centers.

As shown in FIG. 6E the GUI 640 can include a graph indicating the mortality rate based on healthcare center. Each dot in the graph can represent a burn center. The user can provide input into a filtering section 642 in order to filter how information is presented in the graph 640. For example, the user can provide input to filter presentation in the graph based on gender, age, regionality, and/or other factors.

Figure 7A:

FIGS. 7A, 7B, and 7C illustrate example variables used with the disclosed techniques and their corresponding importance indicators. FIG. 7A illustrates a table 700 depicting predictor variables and missingness of such variables. In an illustrative example for determining outcomes of burn patients, 23 predictor variables can be selected for an exemplary analysis. The 23 predictor variables can be selected from over 50 all or partially recorded predictor variables in the illustrative dataset. Predictor variables can be selected on a basis of completeness (e.g., at least 75% complete required) and clinical significance. Cumulatively, as shown in the table 700 of FIG. 7A, 5.1% of data may be missing and 54% of patient records may contain at least one missing value. The disclosed techniques can also be applied to different use cases and to determine different types of patient outcomes for different cohorts of patients. As a result, the identification, selection, and missingness analysis of predictor variables can vary for each of the different use cases. The use case of determining patient outcomes for burn patients is merely an illustrative example and is not intended to be limiting.

FIG. 7B illustrates a table 710 depicting similarity of imputed values to ground truth for categorical (top) and continuous (bottom) variables during an imputation process as described herein (e.g., refer to FIG. 2). For all metrics, higher values may indicate better agreement with ground truth measurements. N shown in the table 710 can be a number out of a total quantity of patient records (e.g., patient data) use for the disclosed techniques that were missing a value. In the illustrative example of FIGS. 7A, 7B, and 7C, the total number of records used can be 60,000.

Imputer performance can be validated by taking a subset of complete data (e.g., patient records) and artificially creating missingness in this subset in proportion to a missingness of the whole exemplary dataset, per variable. Then, the computer system 102 can implement an imputer module, which can be trained on this dataset. In addition to calculating traditional outcome metrics (e.g., accuracy and F1 score for categorical variables, Pearson's r and Spearman's rho for continuous variables), categorical variables distributional similarity can be measured between imputed and actual values. A KLD ratio, for example, can be calculated, for the exemplary dataset, as 1 minus a ratio of Kullback-Leibler divergence between the imputed and actual distribution to the Kullback-Leibler divergence of the modal value imputation to the actual value. Thus, a positive value may indicate that the imputation process performed better than imputing the most frequently occurring value(s). The imputation techniques described herein can produce improved results and increase performance on datasets.

FIG. 7C is a table 720 depicting feature importance for mortality prediction and a table 730 depicting feature importance for LOS prediction. The units in this particular example are abstract. One or more other units of measurement can also be used. CatBoost modeling can calculate feature importance by measuring an extent to which changing predictor variables may change outcome variables. Importance values can be normalized to sum to a value (e.g., numeric, integer) of 100. Some variables that may traditionally be assigned high importance (e.g., age, TBSA) can rank highly in the model while other less often employed variables may also play a significant explanatory role. Refer to FIG. 3 for further discussion about the feature importance of various different variables.

Figure 8:
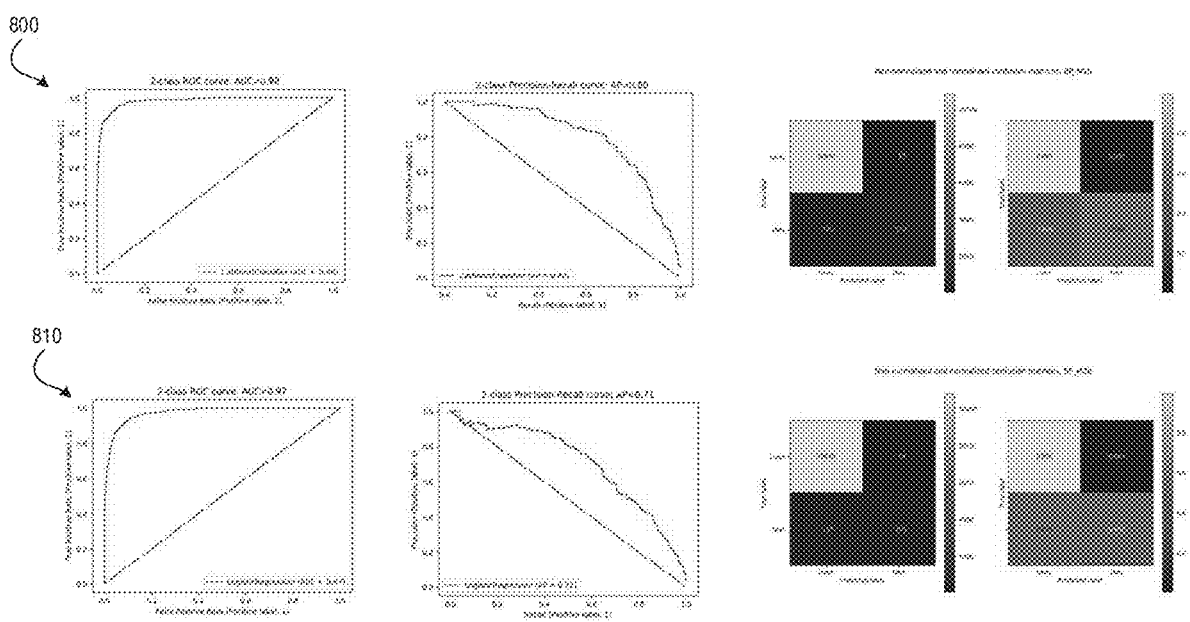
FIG. 8 depicts example mortality prediction (top row) and logistic regression mortality prediction (bottom row) using the disclosed techniques.

FIG. 8 depicts example gradient boosted/CatBoost mortality prediction (top row) graphs 800 and logistic regression mortality prediction (bottom row) graphs 810. The graphs 800 and 810 depict a comparison of 2 types of models: a gradient boosted random forest model (e.g., CatBoost) and a traditional unpenalized logistic regression model. CatBoost modeling can be chosen among other tree-based methods for its support of categorical features (and thus, one-hot encoding may not be needed) and improved performance over other similar methods (e.g., the Scikit-Learn Gradient-Boosted Classifier and XGBoost classifier, etc.). In the case of CatBoost, default model parameters can be used; in particular, a learning rate can be set at 0.03 and a depth to 6. For the logistic regression model, categorical predictor variables can be one-hot encoded.

Using the exemplary dataset described throughout this disclosure, the CatBoost model can achieve a test AUC of 0.986 with an average precision of 0.8, as shown by the graphs 800 in the top row of FIG. 8. The logistic regression, by comparison, can produce an AUC of 0.97 with an average precision of 0.706, as shown by the graphs 810 in the bottom row of FIG. 8. While accuracy is near ceiling for both models, the CatBoost model can be more sensitive, which can lead to an improvement in average precision of predicting model outcomes.

Figure 9:
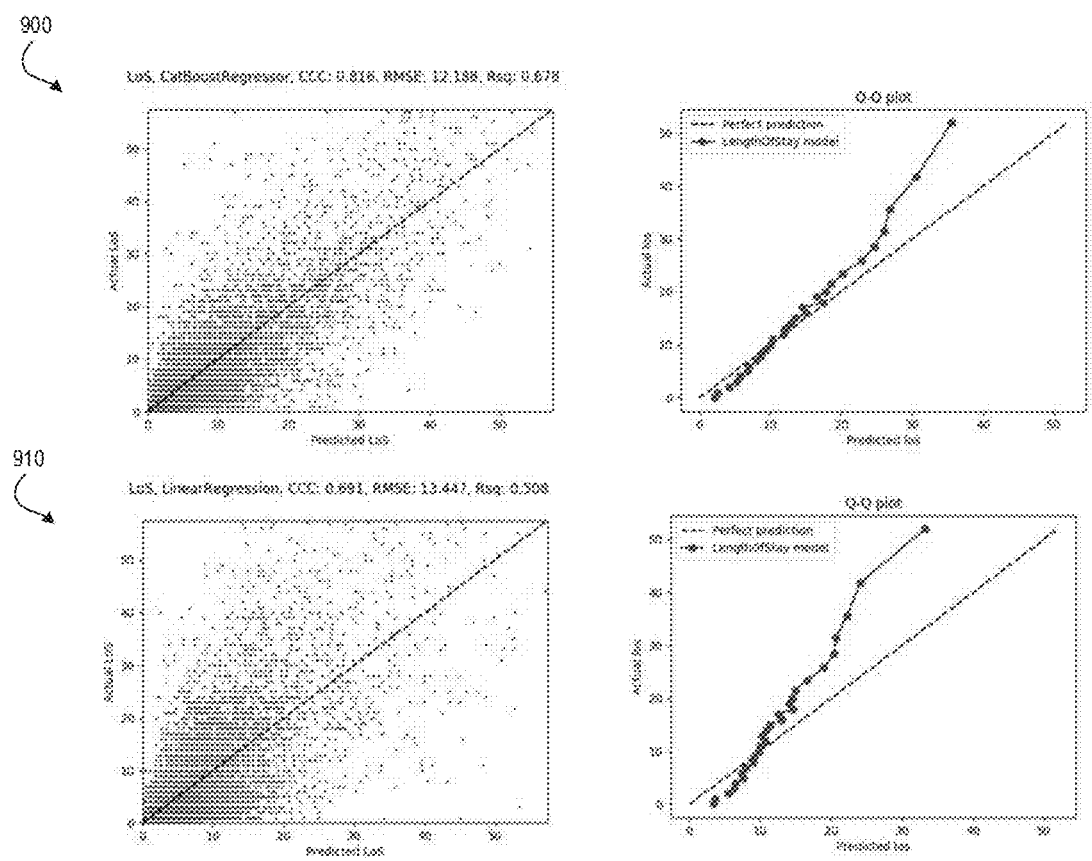
FIG. 9 illustrates length of stay prediction (top row) and linear regression (bottom row), where scatterplots are presented left and quantile-quantile plots are presented right, each dot representing average position of a data quantile.
Figure 10:
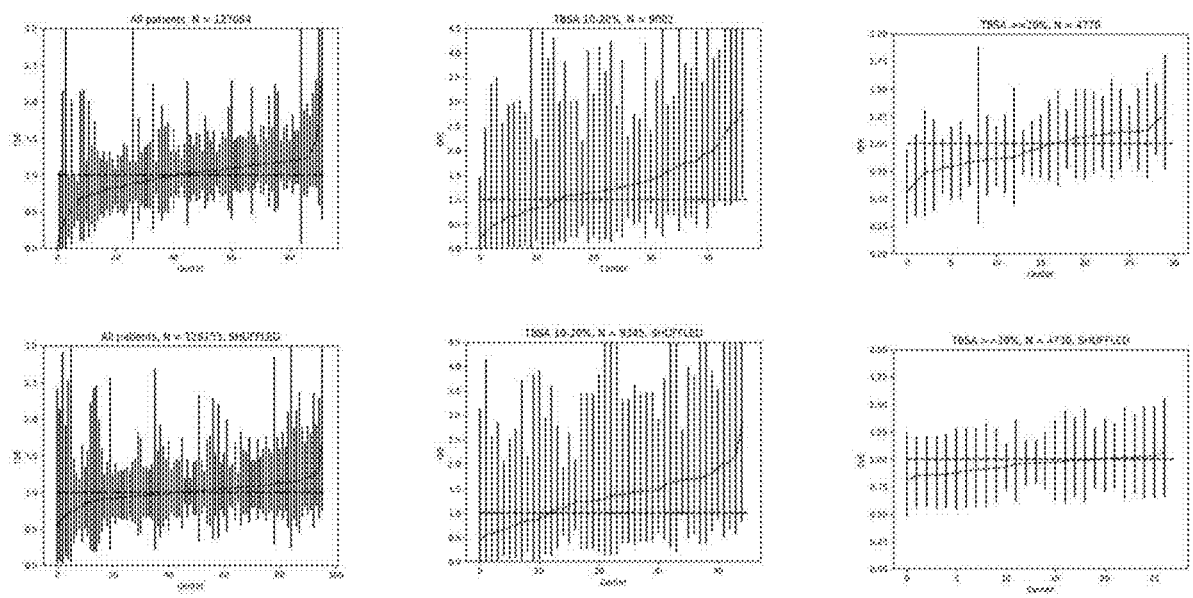
FIG. 10 includes graphical depictions of observed/expected ratios for mortality prediction.
Figure 11:
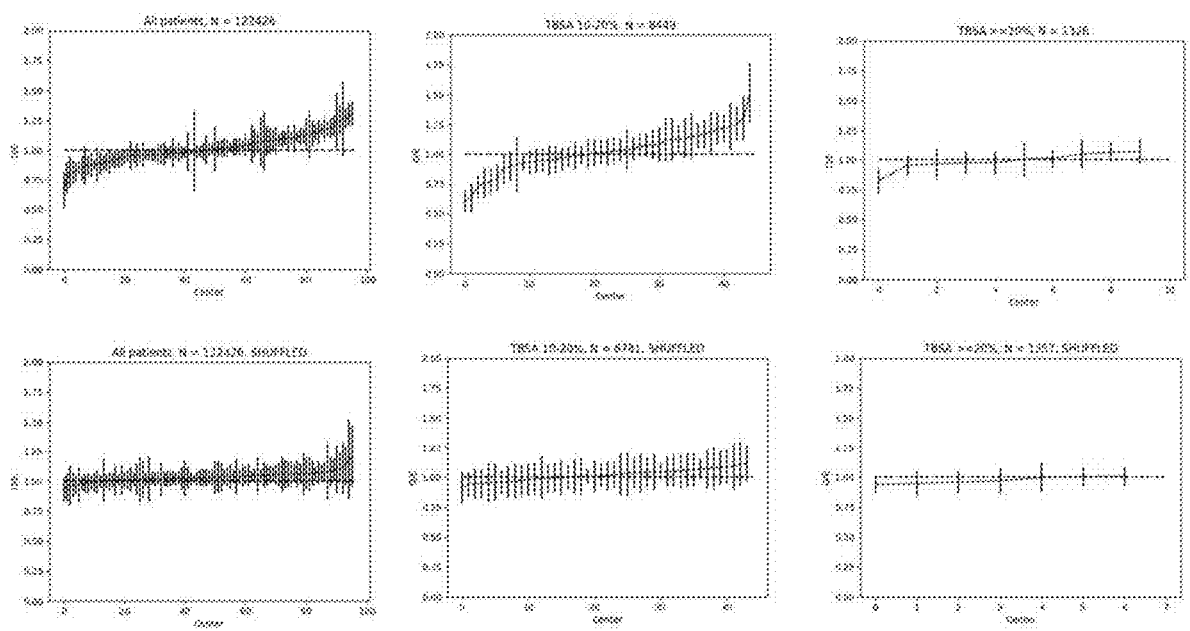
FIG. 11 includes graphical depictions of observed/expected ratios for length of stay predictions.

FIG. 9 illustrates length of stay prediction (top row) graphs 900 and linear regression (bottom row) graphs 910, where scatterplots are presented left and quantile-quantile plots are presented right, each dot representing average position of a data quantile. Analogous to the case of mortality prediction, an unpenalized linear regression (refer to the graphs 910) and the CatBoost regressor (refer to the graphs 900) can be compared to perform LOS prediction on the exemplary dataset described herein. Categorical features can be one-hot encoded for the linear regression model but not for the CatBoost model. Likewise, default parameters can be used for the CatBoost model. $R^2$ and CCC can be measured when the CatBoost model is applied to the test dataset. The CatBoost model may outperform the linear regression model as shown in the FIG. 9. For example, the CatBoost model can achieve, using the exemplary dataset described throughout this disclosure, a test $R^2$ of 0.68, a CCC of 0.82, and an RMSE of 12.1 days. The linear regression model, on the other hand, can achieve a test $R^2$ of 0.51, CCC of 0.69, and an RMSE of 13.4 days. The CatBoost model is more accurate and less biased than the linear regression model for higher and lower LOS durations FIG. 10 includes graphical depictions of observed/expected ratios for mortality prediction. FIG. 11 includes graphical depictions of observed/expected ratios for length of stay predictions. Referring to both FIGS. 10 and 11, CatBoost models can be used for calculating O/E ratios of both mortality and LOS. For each bootstrapped/imputed dataset, the corresponding model can be applied to all data in the dataset to predict mortality and/or LOS. The results can also be filtered by healthcare center and a resulting total expected deaths or days in the center per center can be calculated. For each patient cohort, centers can be filtered out that may have fewer than 100 patients (or another predetermined quantity of patients) and, for mortality prediction, less than 1 expected death (or another predetermined quantity of deaths). Confidence intervals may be critical to O/E analysis, so these can be calculated separately for mortality and LOS predictions, using the same techniques described herein.

The techniques can be as follows: for each dataset, the computer system 102 can calculate confidence intervals using a parametric model. Using bootstrapping, the computer system 102 can identify a median value across datasets for upper and lower bounds of confidence intervals as well as for a mean O/E value. Such median values can be taken to describe an O/E interval. A difference between mortality and LOS model(s) can lay in choice of parametric model. For mortality, a Clopper-Pearson interval can be used, which can approximate a binomial proportion interval and can be valid for large N, which may be the case with some datasets. For LOS prediction, normal distribution can be used as the parametric model.

Using these confidence intervals, 'over-performing' healthcare centers can be identified as those for which an entirety of the confidence interval is below a y=1 line. 'Under-performing' healthcare centers can be those for which an entirety of the confidence interval is above the y=1 line. These are shown in the top graph rows of FIGS. 10 and 11.

In addition, to ensure validity of these techniques and to avoid multiple comparisons error, the technique described above can be repeated by randomly permuting associations between patient and healthcare center. In such a scenario, over- and under-performance may be mitigated, which is depicted in the bottom graph rows of FIGS. 10 and 11.

Figure 12A:
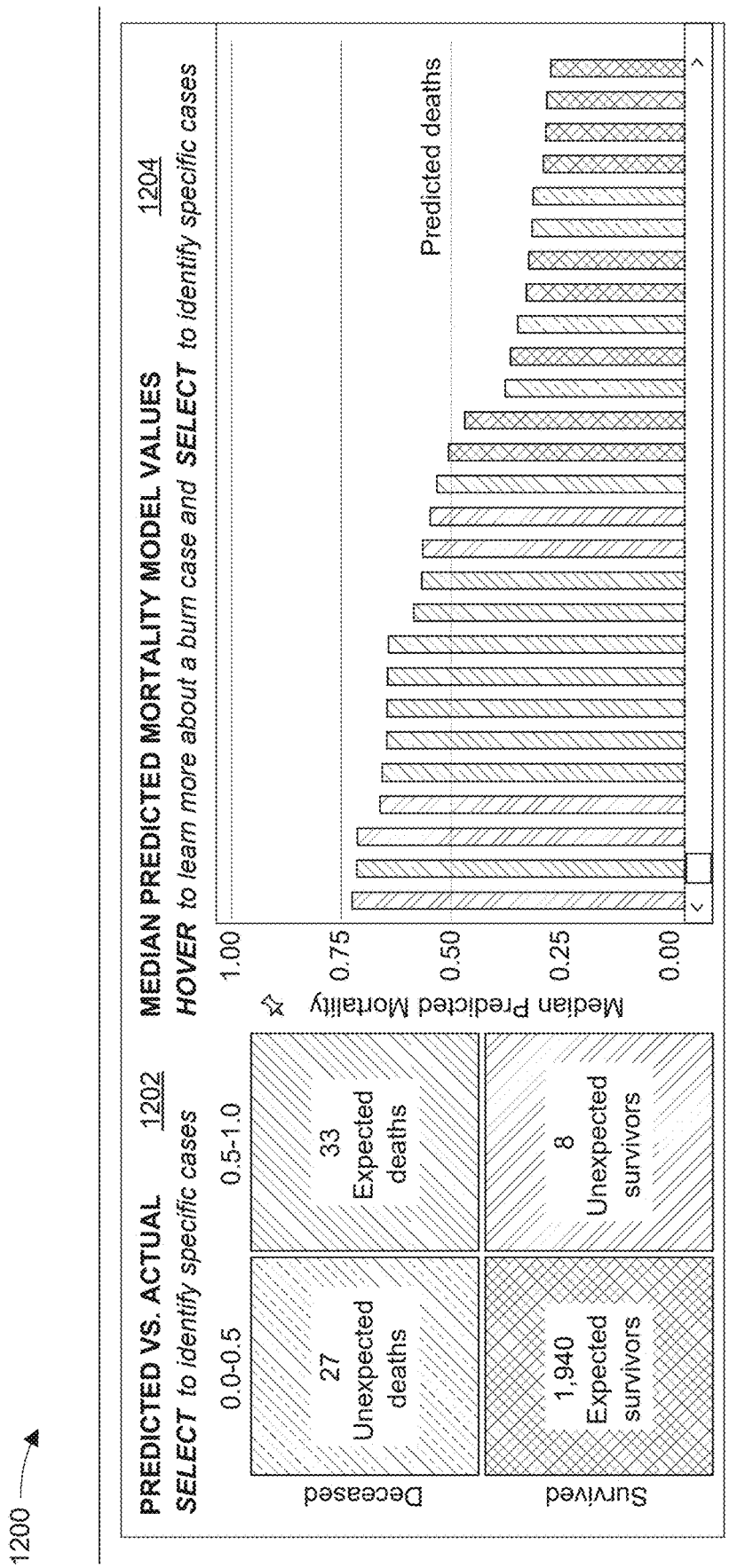
Figure 12B:
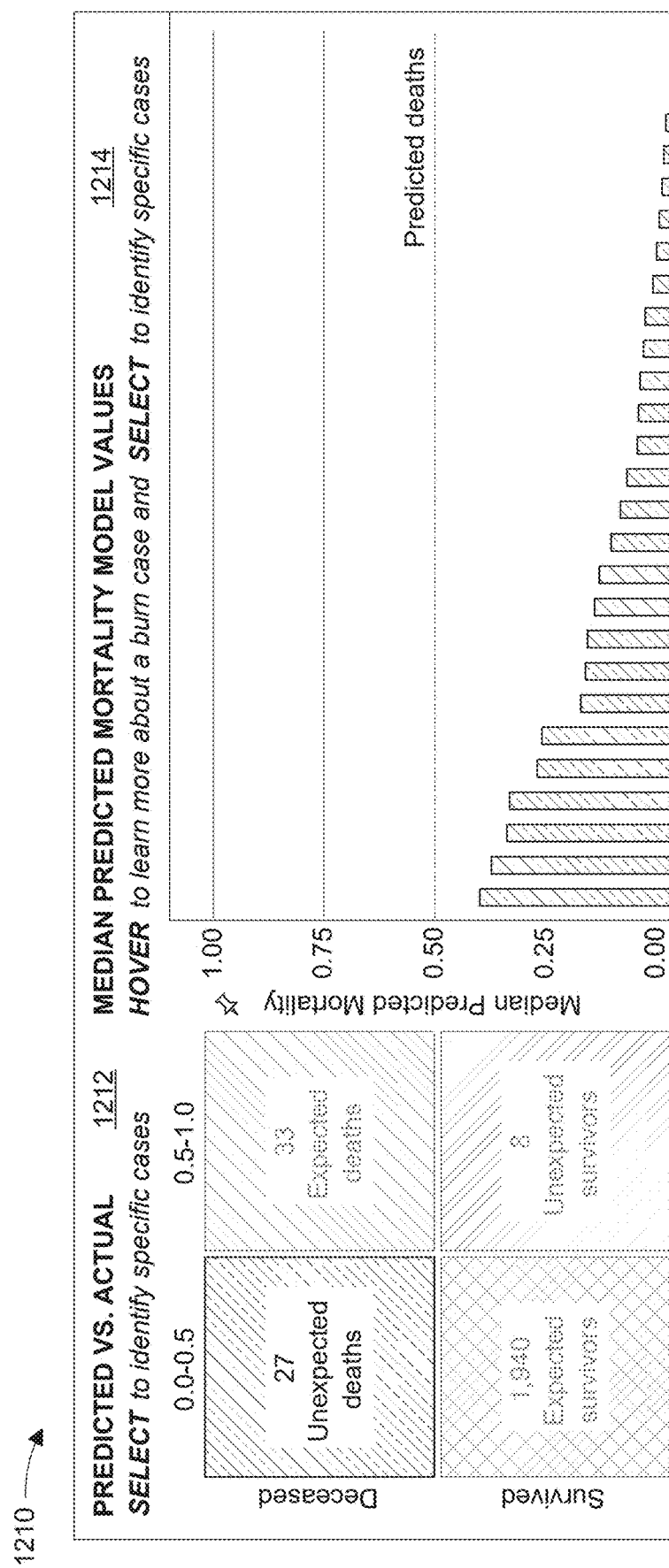

FIGS. 12A, 12B, and 12C illustrate example GUI displays for presenting patient outcomes at a computing device. The computing device can be the user device 104 or any other type of computer system described herein.

FIG. 12A illustrates a GUI 1200 for presenting patient-level mortality outcomes that are determined using the disclosed techniques. The information presented in the GUI 1200 can correspond to a particular healthcare facility and/or a group of healthcare facilities. The GUI 1200 can include a matrix 1202 for visually displaying predicted versus actual patient deaths. Each box in the matrix 1202 can be user-selectable to view additional information about specific cases associated with the selected box. The GUI 1200 can also include a graph 1204 for visually displaying median predicted mortality values. A relevant user can hover over any one or more bars in the graph 1204 to view information about a patient case. Hovering over the bars can cause a pop-out window to be presented in the GUI 1200 and overlay at least a portion of the graph 1200. The user can also select any of the bars in the graph 1204 to view additional information about specific cases associated with the selected bar. Selecting the bars can cause a new GUI to be presented at the computing device.

FIG. 12B illustrates a GUI 1210 for presenting different categories of predicted results versus actual results to identify unexpected deaths. The information presented in the GUI 1210 can correspond to a particular healthcare facility and/or a group of healthcare facilities. The GUI 1210 can include a matrix 1212 for visually displaying predicted versus actual patient deaths. Each box in the matrix 1212 can be user-selectable to view additional information about specific cases associated with the selected box. The GUI 1210 can also include a graph 1214 for visually displaying median predicted mortality model values. A relevant user can hover over any one or more bars in the graph 1214 to view information about a patient case. Hovering over the bars can cause a pop-out window to be presented in the GUI 1210 and overlay at least a portion of the graph 1214. The user can also select any of the bars in the graph 1214 to view additional information about specific cases associated with the selected bar. Selecting the bars can cause a new GUI to be presented at the computing device.

FIG. 12C depicts information that can be displayed in a GUI, similar to the GUIs 1200 and 1210 described above. For example, a table 1220 can be displayed in a GUI to the relevant user to provide information about selected burn injuries (e.g., selected burn or other patient cases). The table 1220 can, in some implementations, be presented in a pop-out window or a new GUI in response to the user selecting or hovering over a box in one of the matrices and/or selecting or hovering over a bar in one of the graphs described in FIGS. 12A and 12B. The table 1220 can also be presented in response to the user providing user input at their computing device to view specific burn or patient cases.

The user can hover over one or more entries in the table 1220 to view additional information 1222 about the hovered-over entry. In some implementations, the user can select one of the entries in the table 1220 in order to view the information 1222 in a separate pop-out window and/or GUI. The information 1222 can indicate additional details about the particular burn patient associated with the hovered-over entry, including but not limited to injury details, outcomes, admission and treatment details, and/or patient details. In yet some implementations, the user can click on or select a given patient to view detailed information, graphs, or other visual depictions described throughout this disclosure about how various features (e.g., characteristics, variables) contributed to a specific outcome predicted for the patient. The user can also view the detailed information to identify patterns in predictors and/or patient outcomes.

Figure 13A:
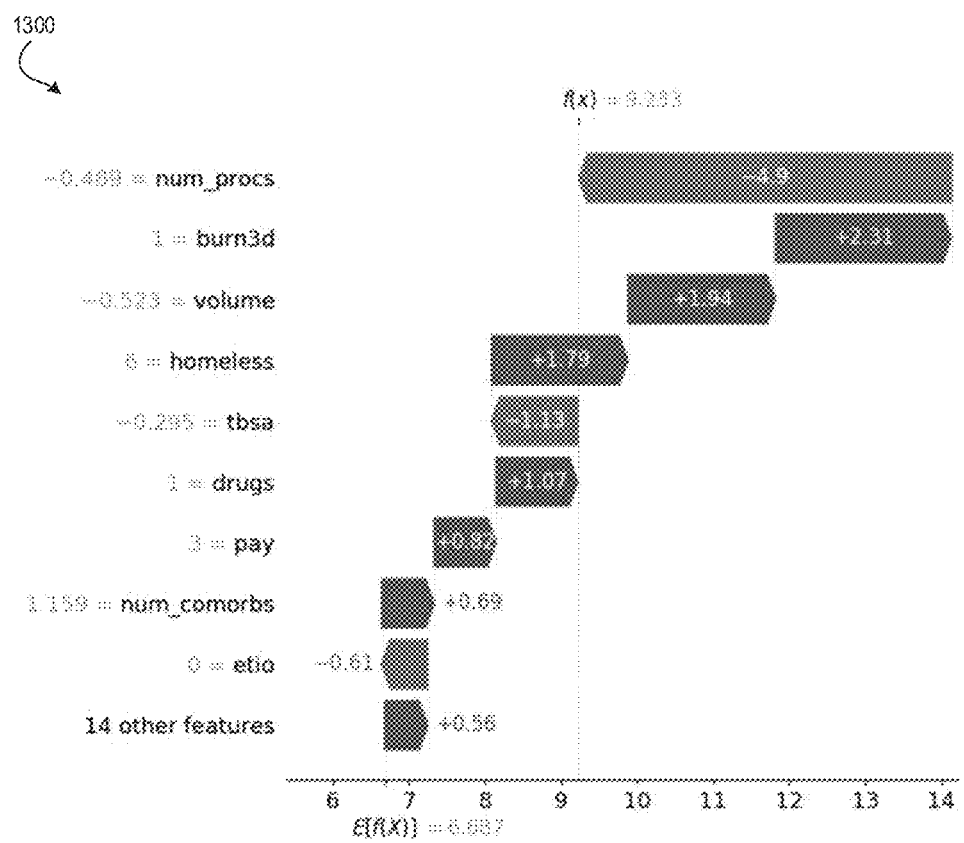
FIGS. 13A, 13B, 13C, and 13D show example Shapley values for predicted patient outcomes.

FIGS. 13A, 13B, 13C, and 13D show example Shapley values for predicted patient outcomes. Graph 1300 in FIG. 13A shows Shapley values for a patient for whom a hospital LOS of 9.2 days was predicted using the disclosed techniques. Analysis performed by the computer system described herein can indicate that an average LOS for patients in a plurality of patient data is approximately 6.687 days. Compared to other patients, a number of procedures that the particular patient in FIG. 13A is undergoing can be fewer than average (e.g., −0.489 standard deviations below mean) and given the importance of that feature to outcome prediction, this patient's duration can be reduced by almost 5 days relative to what it would have been, on that account. On the other hand, presence of third-degree burn (burn3d), relatively low volume of the center the patient was treated at (volume) and absence of homelessness status (homeless=6) can increase the predicted duration for the particular patient. Therefore, the graph 1300 indicates how various weights can be applied to the features/variables used in predicting patient outcomes based on the features/variables respective importance.

Figure 13B:
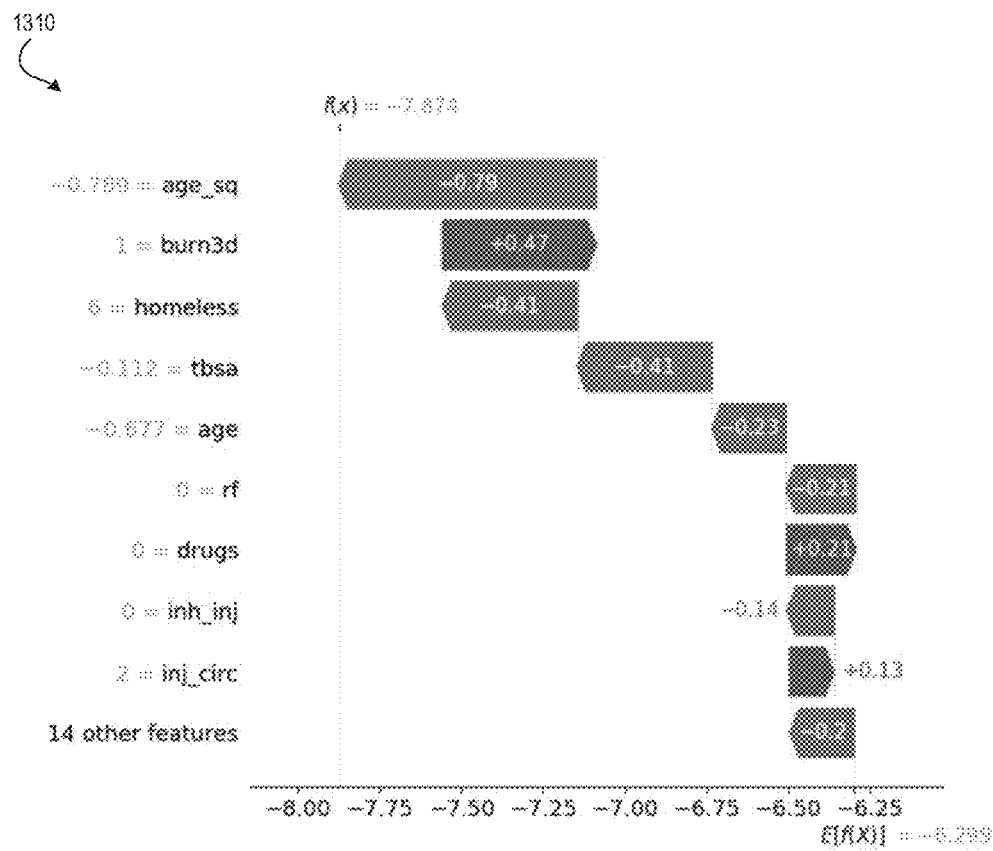

Graph 1310 in FIG. 13B shows Shapley values for a patient whose log odds ratio is −7.874, corresponding to a predicted mortality probability of approximately 0.003. CatBoost model outputs log odds (e.g., logits), rather than probabilities. This is done in order to have an output range defined over an entire negative number line rather than just [0, 1]. The formula $\exp(X)/(1+\exp(X))$ can be used to convert logits back to probabilities. Otherwise, once converted to probabilities, interpretation is similar as described in reference to the graph 1300 in FIG. 13A.

Figure 13C:
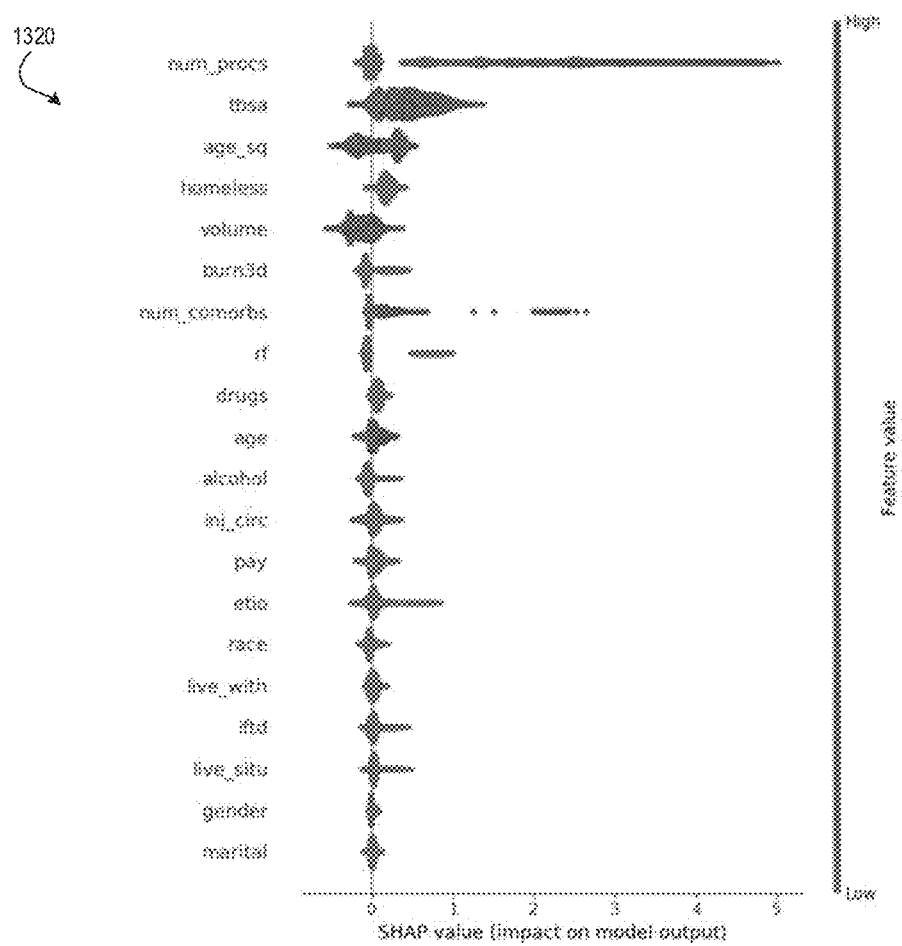

Graph 1320 in FIG. 13C shows overall feature impact on LoS predictions. Values can be depicted in gray for features where 'high' and 'low' list not defined, e.g. variables with categorical values. Shapley values may provide valuable population-level insight. The graph 1320 indicates not only distribution of Shapley values (for LoS predictions in this example) but also a relationship between the feature value (where that feature is numeric) and the Shapley values.

Figure 13D:
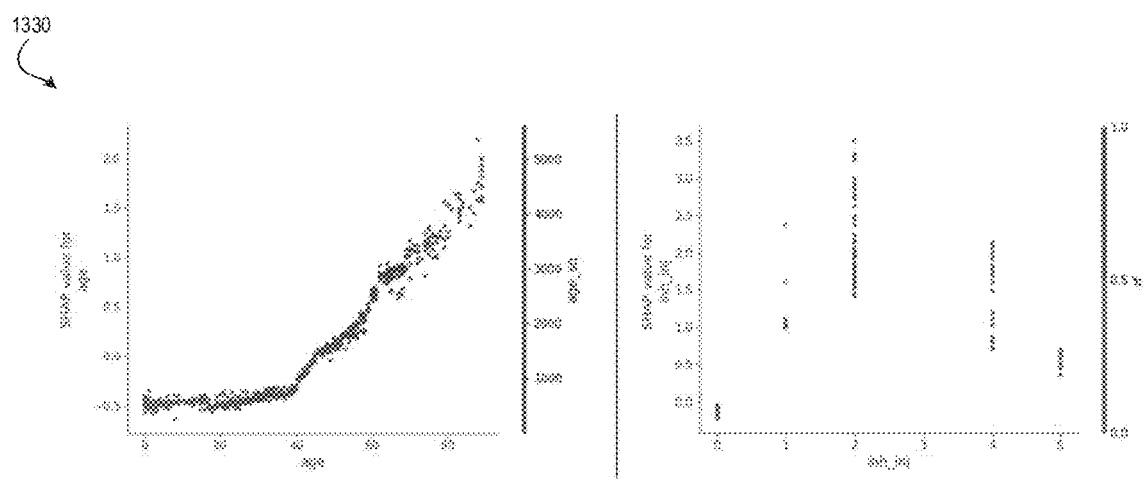

Graphs 1330 in FIG. 13D show Shapley values for age (left) and inhalation injury (right), for a mortality model. Inhalation injury values can be coded as follows: 0: 'No', 1: 'Yes, without cutaneous burn injury', 2: 'Yes with cutaneous burn injury', 3: 'Not known/Not recorded', 4: 'Yes without cutaneous burn injury', 'Not applicable.' The graphs 1330 provide a fine-grained view of a relationship between feature value and Shapley value, and in particular accommodate a non-numeric nature of categorical variables. On the right of each subplot is a related feature, which can be color-coded (e.g., pattern-coded, etc.) to provide additional information about relationships in the data.

FIGS. 14A, 14B, 14C, and 14D illustrate results of comparing burn patient fluid therapy across a plurality of healthcare centers. The comparisons shown can be used by healthcare centers to drive quality improvement since the centers can review their distribution of patients by fluid therapy against other healthcare centers and identify ways in which to improve their fluid therapy. The data used and shown in FIGS. 14A, 14B, 14C, and 14D is merely illustrative. The techniques and visuals described herein can also be used to assess the healthcare centers according to various different variables, features, and/or treatment plans, not just fluid therapy.

Figure 14A:
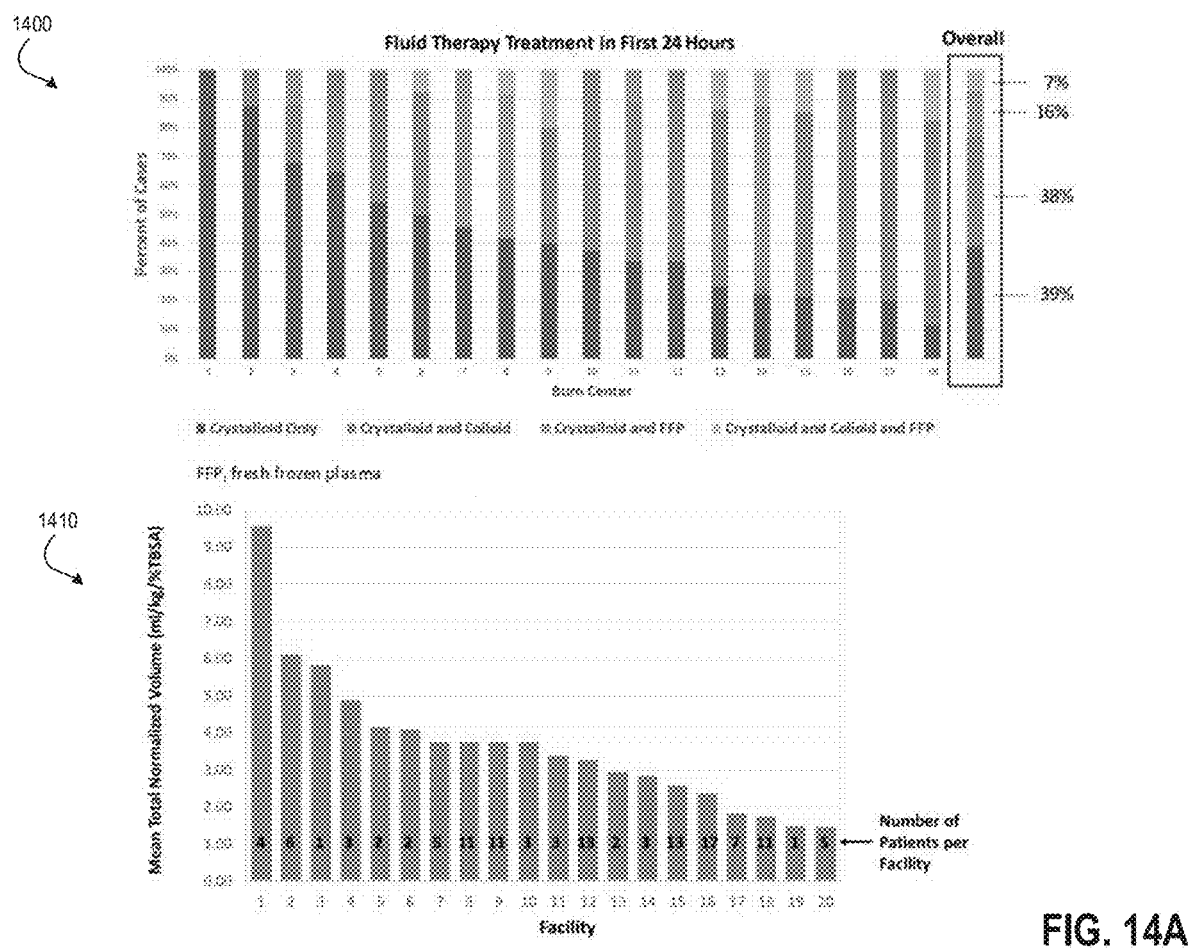
FIGS. 14A, 14B, 14C, and 14D illustrate results of comparing burn patient fluid therapy across a plurality of healthcare centers.

The percentages of patients by fluid therapy for each healthcare center with 5 or more cases and overall are shown in graph 1400 of FIG. 14A. Overall, 39% of patients received crystalloids only, 38% received crystalloids and colloids, 16% received crystalloids and FFP, and 7% received crystalloids, colloids, and FFP. The graph 1400 shows substantial variation among healthcare centers in proportions of patients receiving those fluid therapies with centers 1 and 2 having very high proportions of patients receiving crystalloids only and centers on the right side of the graph 1400 having high proportions of patients receiving crystalloids and colloids. Centers 7, 8, and 14 had relatively high proportions of patients receiving crystalloids and FFP while relatively low proportions of patients received crystalloids, colloids, and FFP.

Graph 1410 in FIG. 14A shows mean normalized crystalloid volume for patients who received crystalloids only 24 hours pre- and in-hospital by healthcare center. The means ranged from 1.46 to 9.58 to ml/kg/% TBSA showing substantial variation among healthcare centers. The number of patients per center ranged from 1 to 17.

Figure 14B:
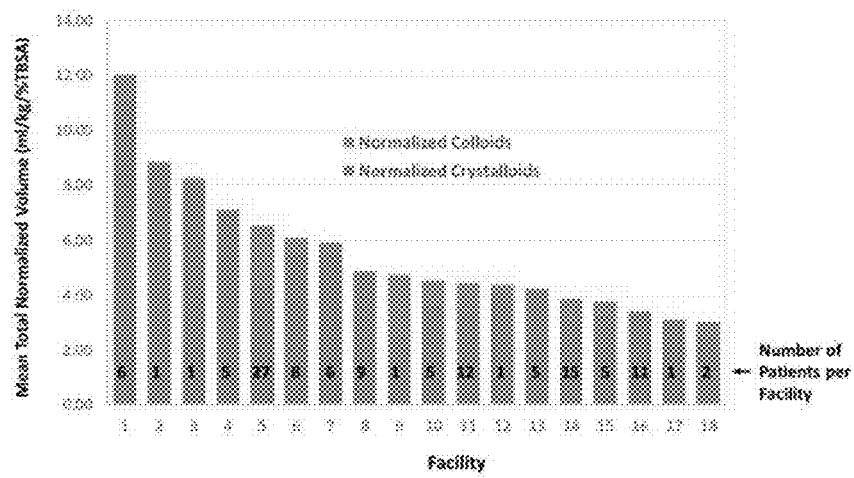
Figure 14B:
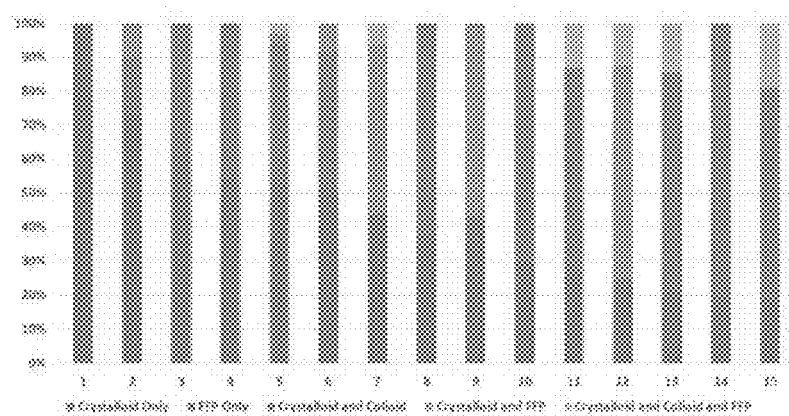

A stacked bar chart 1420 in FIG. 14B shows combined normalized crystalloid and colloid volumes for patients who received crystalloids and colloids only 24 hours pre- and in-hospital by healthcare center. Crystalloids accounted for a majority of the volume in all centers and the total combined volume ranged from 3.05 to 12.02 ml/kg/% TBSA with notable variability across centers. The number of patients per center ranged from 1 to 27.

Graph 1430 in FIG. 14B shows percentages of patients by fluid type 24 hours in-hospital by center for those centers with 10 or more cases. The distribution of patients by fluid types is similar to that shown in the graph 1410 in FIG. 14A, which was for healthcare centers with 5 or more cases. The graph shows substantial variation among centers in the proportions of patients receiving those fluid therapies with centers 1 and 2 having very high proportions of patients receiving crystalloids only and centers on the right side of the graph generally having high proportions of patients receiving crystalloids and colloids. Centers 7, 9, and 12 had relatively high proportions of patients receiving crystalloids and FFP while relatively low proportions of patients received FFP only or crystalloids, colloids, and FFP.

Figure 14C:
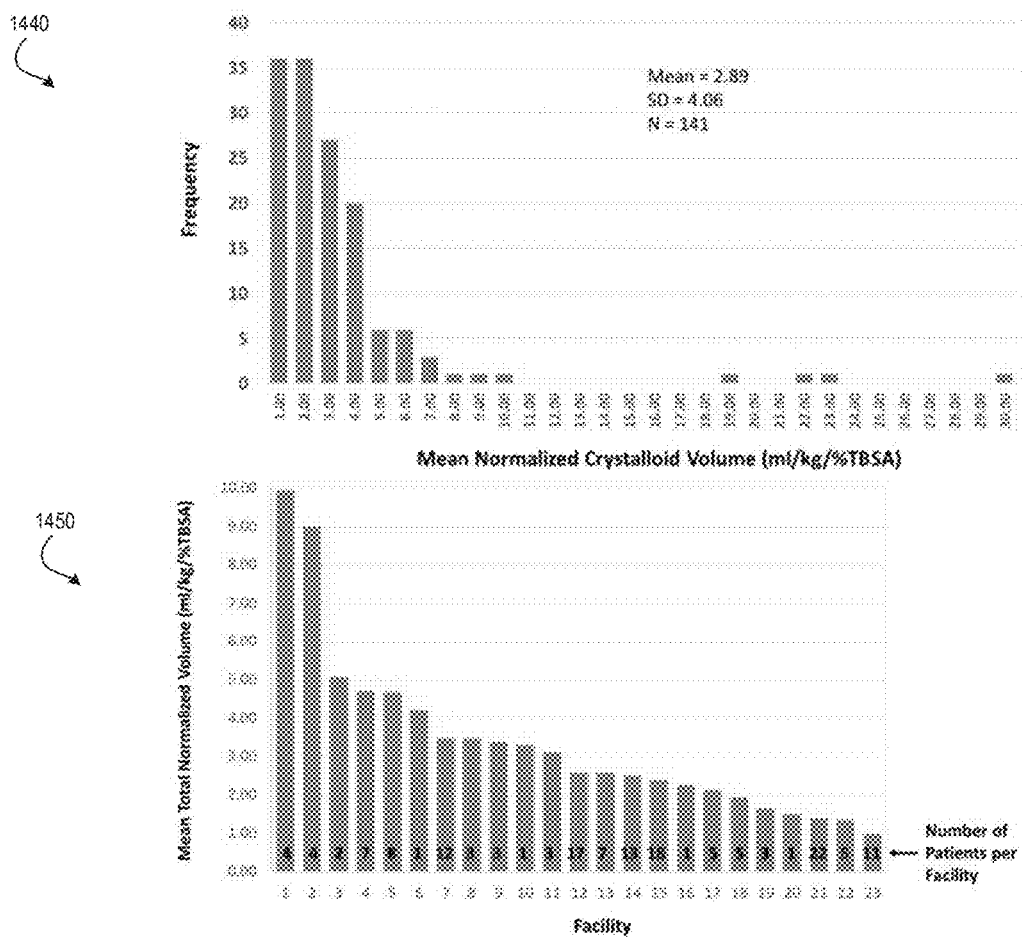

Frequencies for mean normalized crystalloid volumes 24 hours in-hospital for patients receiving crystalloids only are shown in graph 1440 in FIG. 14C. This distribution is heavily right-skewed with the majority (84%, n=119) of patients receiving less than 5.0 ml/kg/% TBSA of crystalloids. The overall mean was 2.89 ml/kg/% TBSA and values ranged from less than 1.0 to 30.2 ml/kg/% TBSA.

Graph 1450 in FIG. 14C shows mean normalized crystalloid volume 24 hours in-hospital for patients receiving crystalloids only by healthcare center. This distribution is similar to that in the graph 1440, which was for 24 hours pre- and in-hospital. In this case, the means ranged from 0.99 to 9.94 to ml/kg/% TBSA with substantial variation among healthcare centers. The number of patients per center ranged from 1 to 22.

Figure 14D:
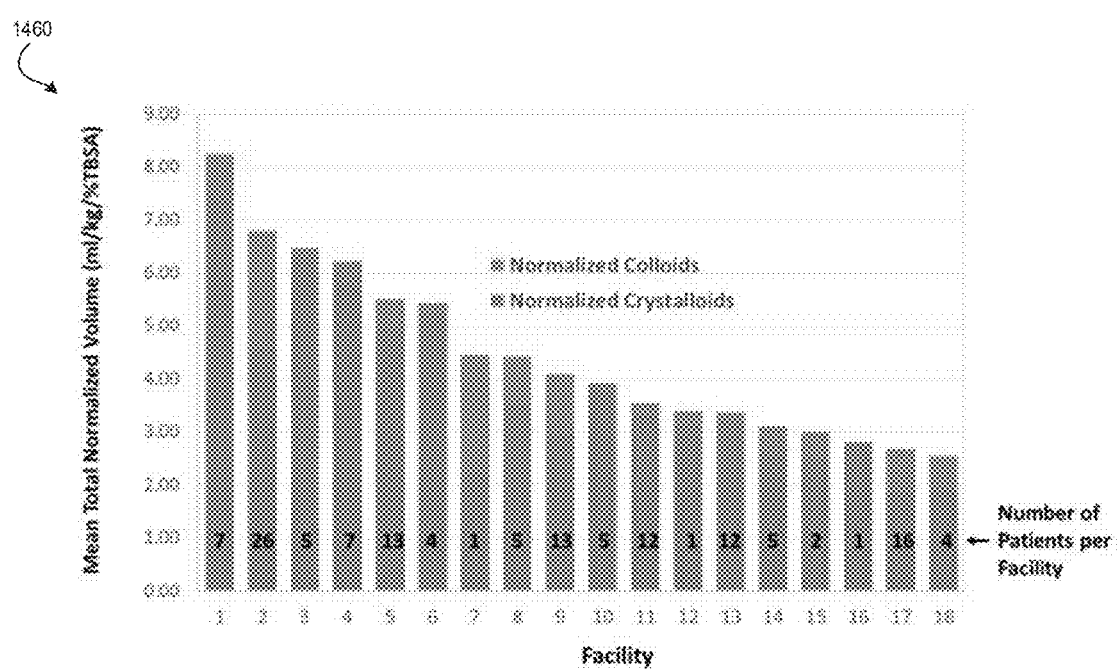

A stacked bar chart 1460 in FIG. 14D shows combined normalized crystalloid and colloid volumes for patients who received crystalloids and colloids only 24 hours in-hospital by healthcare center. This distribution is similar to that shown in the chart 1420 in FIG. 14B, which is for 24 hours pre- and in-hospital. Crystalloids accounted for a majority of the volume in all healthcare centers except center 7 and the total combined volume ranged from 2.55 to 8.24 ml/kg/% TBSA with notable variability across the centers. The number of patients per center ranged from 1 to 26.

FIGS. 15A, 15B, 15C, and 15D, 15E, and 15F illustrate example GUIs for viewing patient outcomes and care at a particular healthcare center. Using the GUIs of FIGS. 15A-F, a relevant user can view information specific to their particular healthcare center, such as an overview of conditions at the center, information organized and/or assessed based on demographics, injury information, and/or patient outcomes. The GUIs of FIGS. 15A-F can also include filters to allow the user more interaction and patient cohort analysis with the patient outcomes that are generated using the disclosed techniques. For example, the user can filter information based on admission year, patient age in years, burn size group, missing status, etc. When the user sets the filters in one of the GUIs in FIGS. 15A-F, the filters can persist and remain in use as the user toggles and switches between GUIs. Therefore, the user may not have to re-enter filter criteria each time they view a new GUI or otherwise change GUIs.

Figure 15A:
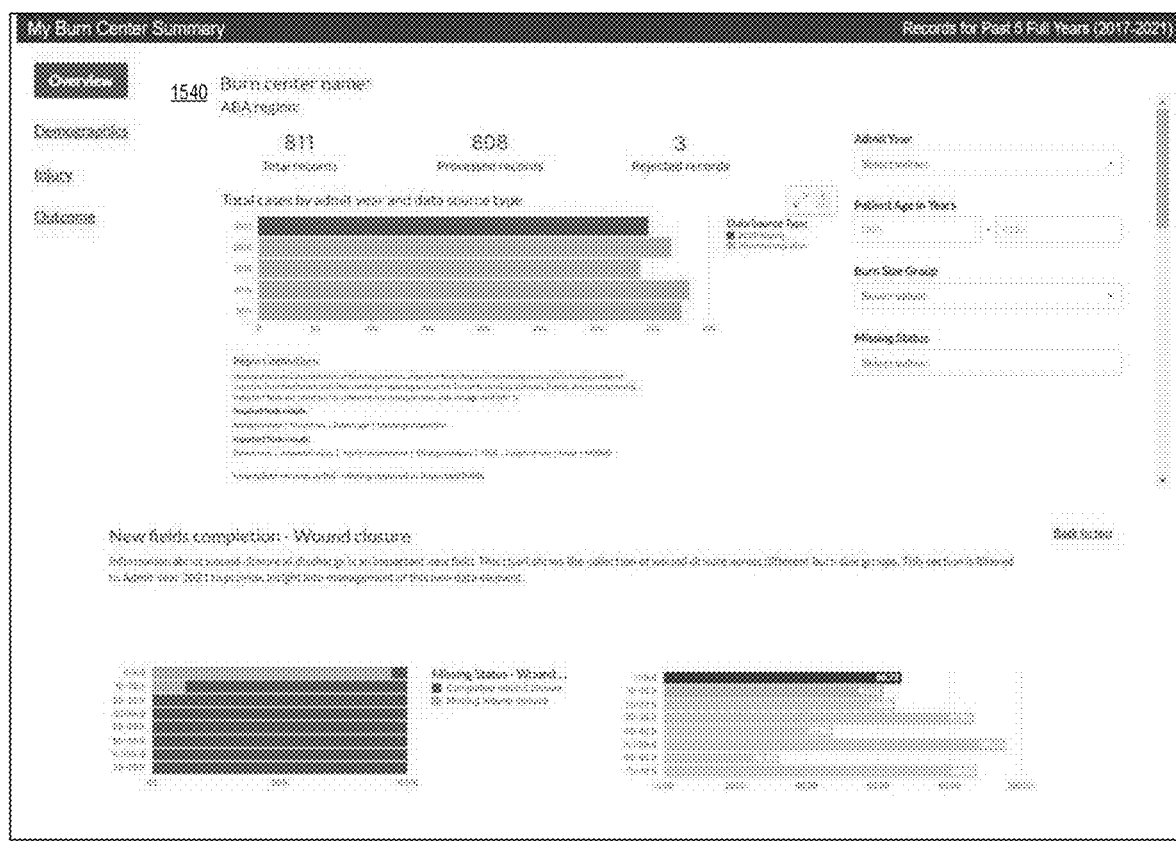

GUI 1500 in FIG. 15A illustrates an overview of information for a particular burn center. The GUI 1500 indicates a summary of patient cases over a predetermined amount of time that have been assessed using the disclosed techniques. In this illustrative example, patient cases have been assessed within a range of 5 years (between 2017-2021). 811 patient data records were processed, 808 of those records were processed, and 3 of those records were rejected. The GUI 1500, as shown with a bar graph or other graphical or visual indication, also indicates a total number of cases admitted each year and a data source type for the predetermined period of time.

The GUI 1500 also presents graphical and/or other visual elements to indicate information about wound closure at discharge from the center for the predetermined period of time. The illustrative examples in the GUI 1500 indicate wound closures across different burn size groups. In some implementations, the information presented in the GUI 1500 can be filtered using the filters described above, such as viewing only patients that were admitted in the year 2021.

Figure 15B:
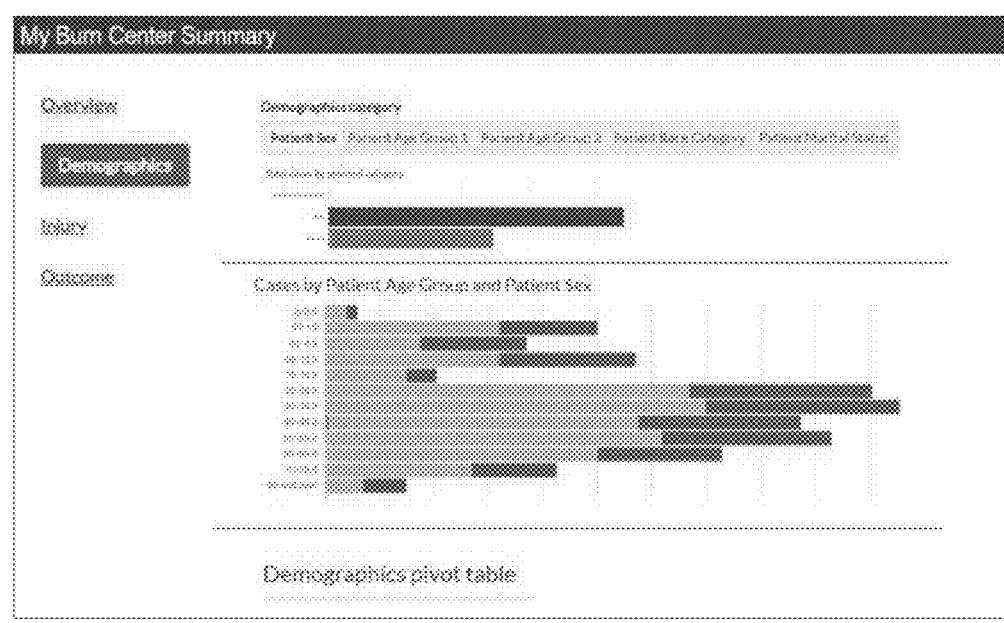

GUI 1520 in FIG. 15B illustrates an overview of information presented based on demographics. The user can toggle between one or more different demographics categories to view updated information in the GUI 1520. In the example of FIG. 15B, the user has selected 'Patient Sex' as the demographics category and therefore the information presented in the GUI 1520 is visualized based on patient sex. The GUI 1520 can visualize patient outcomes in various different types of graphical and/or visual elements, charts, tables, and/or graphs. The patient outcomes can be presented based on patient age and/or patient sex and/or by injury location (e.g., in a map, in a chart, state-level, county-level, town-level). The patient outcomes can additionally or alternatively be presented with a demographics pivot table, which can be a detailed chart based on patient age, patient race, patient sex, and/or one or more other demographic categories.

Figure 15C:

GUI 1530 in FIG. 15C illustrates an overview of information presented based on injury for the particular healthcare center. One or more of the visuals and/or graphical elements presented in the GUI 1530 can indicate data completeness gaps. The filters described herein can also be used to filter analysis presented in the GUI, including but not limited to burn injuries, including burn size, inhalation injury, circumstance of injury, and/or place of injury occurrence.

The GUI 1530 also can present visualizations of patient cases by different etiology categories using circle charts or other types of graphical elements and visualizations. The GUI 1530 can present a table of cases by etiology, patient age, and/or one or more other filtering categories or demographic categories described herein. The table can be used to provide more detailed (and selectable/expandable) information about different etiology categories and/or view case mixes by age groups or other filtering categories.

Figure 15D:
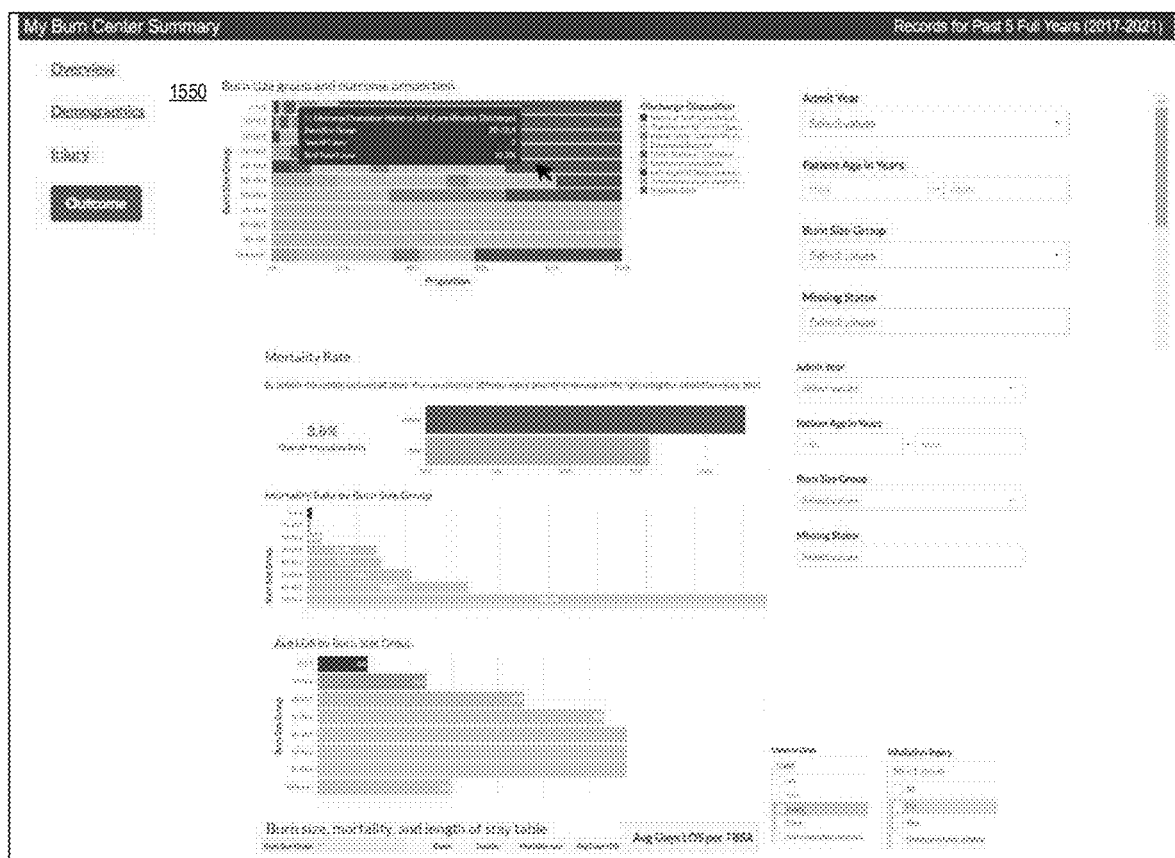

GUI 1550 in FIG. 15D illustrates an overview of information presented based on patient outcome for the particular healthcare center. The patient outcomes can be presented in a variety of different types of graphical and/or visual elements, including but not limited to graphs, bar graphs, or other types of charts and/or tables. Each of the graphical and/or visual elements can also be user-interactive. For example, the user can hover over a portion of a graph to view additional details about the particular patient and/or information of interest. The additional details can be presented in a pop-out window that may visually overlay at least a portion of the graph or other information presented in the GUI 1550, as shown in FIG. 15D. In some implementations, the user can select the portion of the graph to cause another GUI to be loaded and presented with the additional details about the information of interest to the patient.

The GUI 1550 can present information about patient mortality rates in graphical and/or visual elements. For example, the user can analyze mortality data and/or view overall mortality, mortality across patient sex, mortality by burn size, and/or mortality by one or more user-identified filtering categories and/or demographic categories. In some implementations, the user can select multiple filtering categories to add additional interactivity and deeper analysis for presentation in the GUI 1550. In the example of FIG. 15D, for example, the user has selected the filter of "Inhalation injury."

The GUI 1550 can additionally or alternatively present information about average hospital LOS in graphical and/or visual elements. A default filter or filters can be applied to the data presented regarding the average hospital LOS. For example, a survivors filter can be applied as default. The user can also select one or more other filters described herein to filter and view the average hospital LOS data.

Moreover, in some implementations of the GUI 1550 in FIG. 15C, the user can view the patient outcomes in a table, which may include one or more benchmark/comparison standards (e.g., average days LOS per TBSA).

Figure 15E:
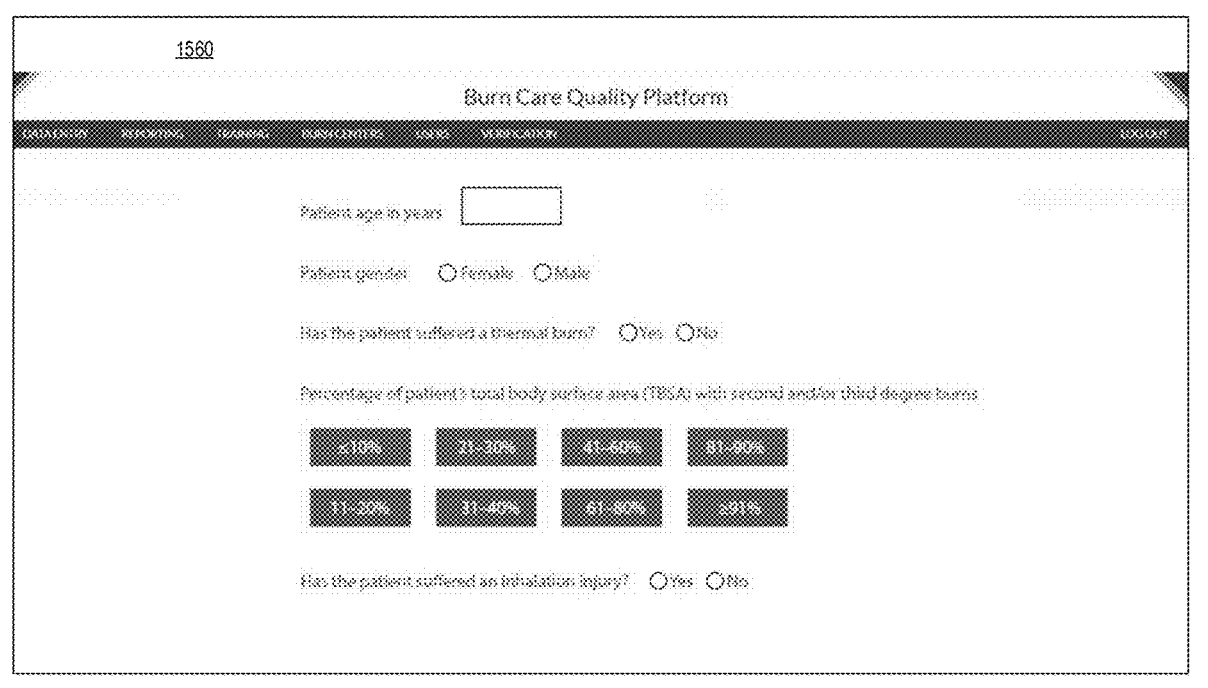
Figure 15F:
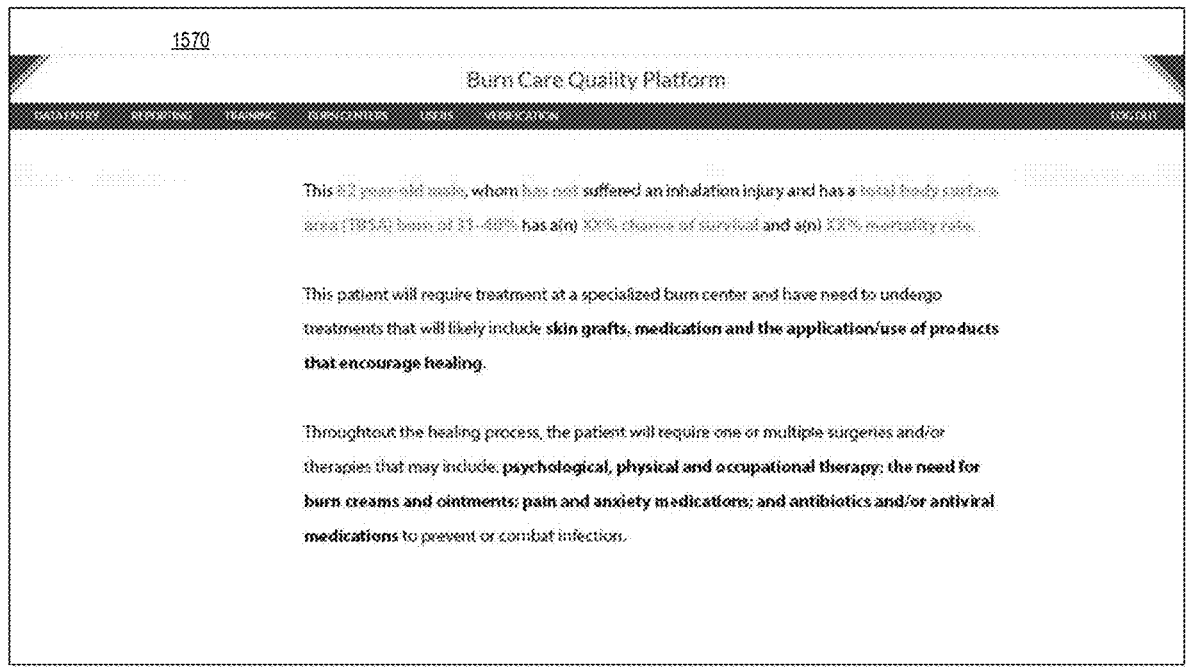

GUI 1560 in FIG. 15E and GUI 1570 in FIG. 15F illustrate a burn risk calculator that can take model output (e.g., predicted patient outcomes) and present the model output back to the relevant user to support patient and/or caregiver decisions and/or discussions. More specifically, the GUI 1560 in FIG. 15E can include one or more text input fields or other types of input fields (e.g., radio buttons, drop down menus, buttons) for receiving input from relevant users, such as caregivers or other healthcare professionals. The relevant user can provide input such as a patient age in years, a patient gender, whether the patient suffered a thermal burn, a percentage of the patient's total body surface area with second and/or third degree burns, and/or whether the patient suffered an inhalation injury. One or more other types of information can be requested and/or provided at the GUI 1560. Any of the inputs received at the GUI 1560 can be processed by the computer system described herein to determine and present patient outcomes that have been predicted using the disclosed modeling techniques. The patient outcomes can be presented in the GUI 1570 depicted in FIG. 15F. As an illustrative example, the GUI 1570 presents information such as a predicted chance of survival and/or mortality rate for a patient having the conditions that are provided as input in the GUI 1560 in FIG. 15E. The GUI 1570 can also present information such as one or more recommended care actions for the patient having the conditions that are provided as input in the GUI 1560 in FIG. 15E.

FIGS. 16A, 16B, 16C, 16D, 16E, and 16F illustrate example GUIs for viewing comparisons and benchmarking of patient outcomes and care across a plurality of healthcare center. The GUIs of FIGS. 16A-F can be used by a relevant user described herein to compare their particular healthcare center to one or more other healthcare centers. The GUIs 16A-F can present benchmarking information based on one or more of the following: overview summary, volume, case mix, LOS, outcome, and/or mortality.

Figure 16A:
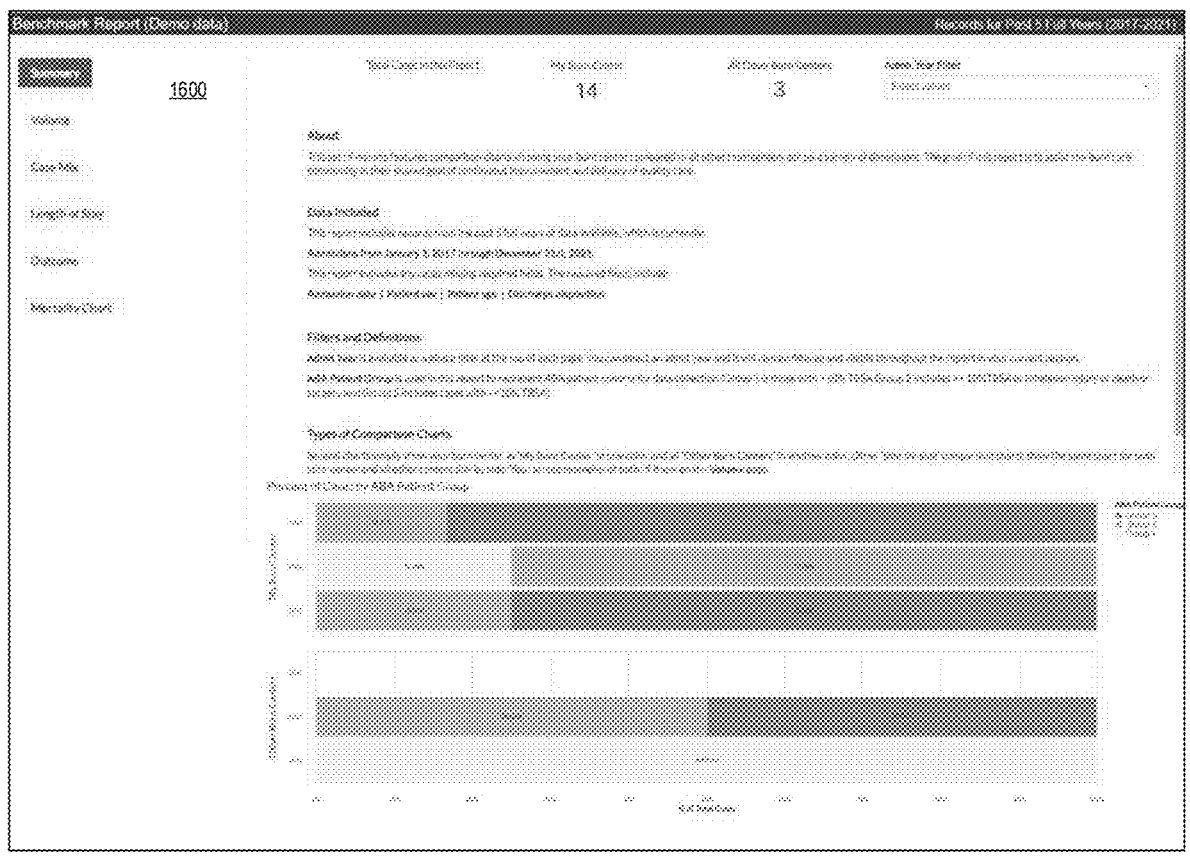
FIGS. 16A, 16B, 16C, 16D, 16E, and 16F illustrate example GUIs for viewing comparisons and benchmarking of patient outcomes and care across a plurality of healthcare centers.

GUI 1600 in FIG. 16A illustrates a summary overview for benchmarking the healthcare centers. The GUI 1600 can include a filtering option for the user to select what year of patient admission for which to filter the data comparisons. As described in reference to FIGS. 15A-D, once the user selects the filter, the filter is applied to all reporting GUIs shown in FIGS. 16A-F. Therefore, the user does not have to reselect the filter every time that they navigate to another GUI or otherwise toggle between GUIs.

The GUI 1600 can present one or more graphical and/or visual elements indicating volume of cases across the healthcare centers (including the healthcare center associated with the user). For example, percent of cases by ABA patient group can be outputted and visually displayed in the GUI 1600. Volume of cases for the particular healthcare center associated with the user can be presented in one graphical depiction while volume of cases for other healthcare centers can be presented in a separate, other graphical depiction. In some implementations, the volume of cases for all the centers can be presented in a singular graphical depiction. In yet some implementations, the volume of cases information can be presented in a separate GUI.

Figure 16B:
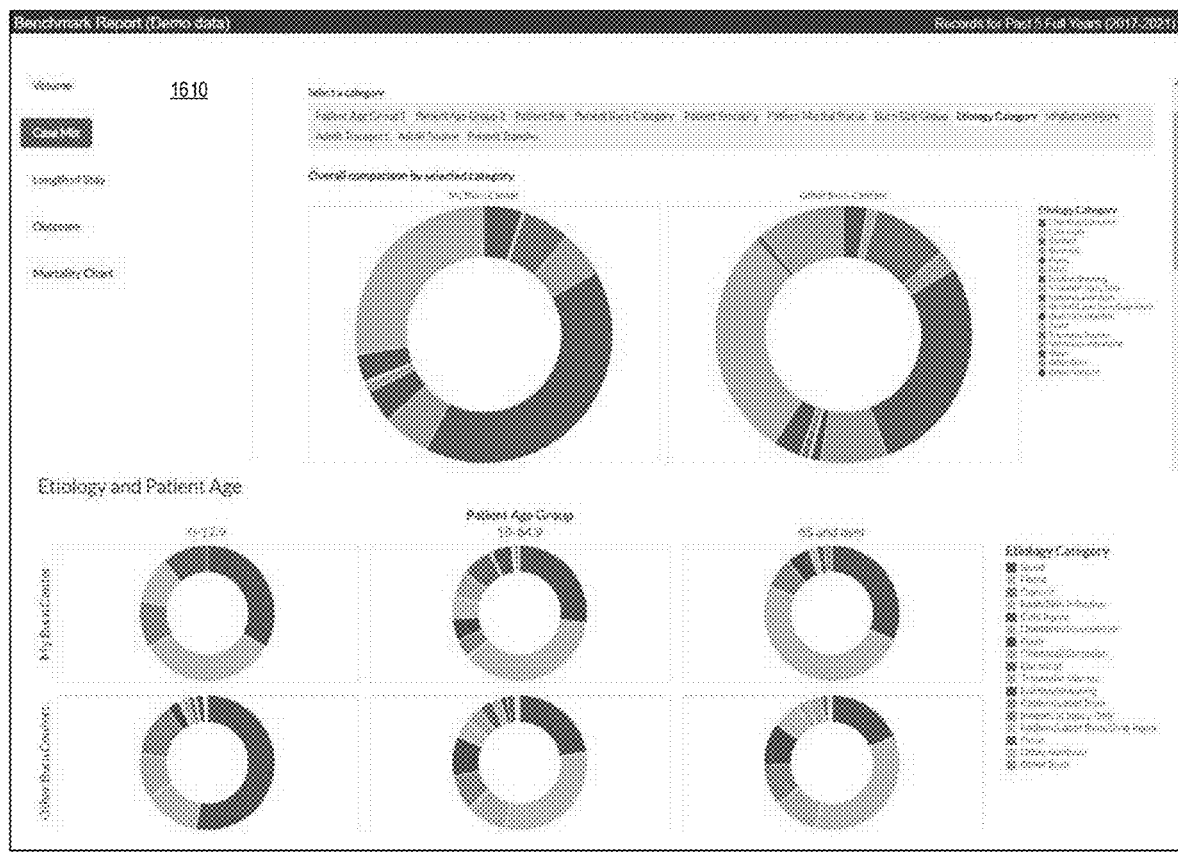

GUI 1610 in FIG. 16B illustrates case mix information for the particular healthcare center and the other healthcare centers. The user can select one or more different categories for visualizing the particular healthcare center's cases compared to other centers. In the example of FIG. 16B, the user has selected an 'Etiology category,' which causes various color-coded (or other visual-identification-coded) circle graphs to be displayed in the GUI 1610. Each portion of the circles graphs may represent a different etiology category. One or more circle graphs can display the cases for the particular healthcare center while one or more other circle graphs can display the cases for the other healthcare centers. The user can also select one or more filtering categories to view different case information in the GUI 1610. In the illustrative example of FIG. 16B, the cases are displayed based on etiology and patient age.

Figure 16C:
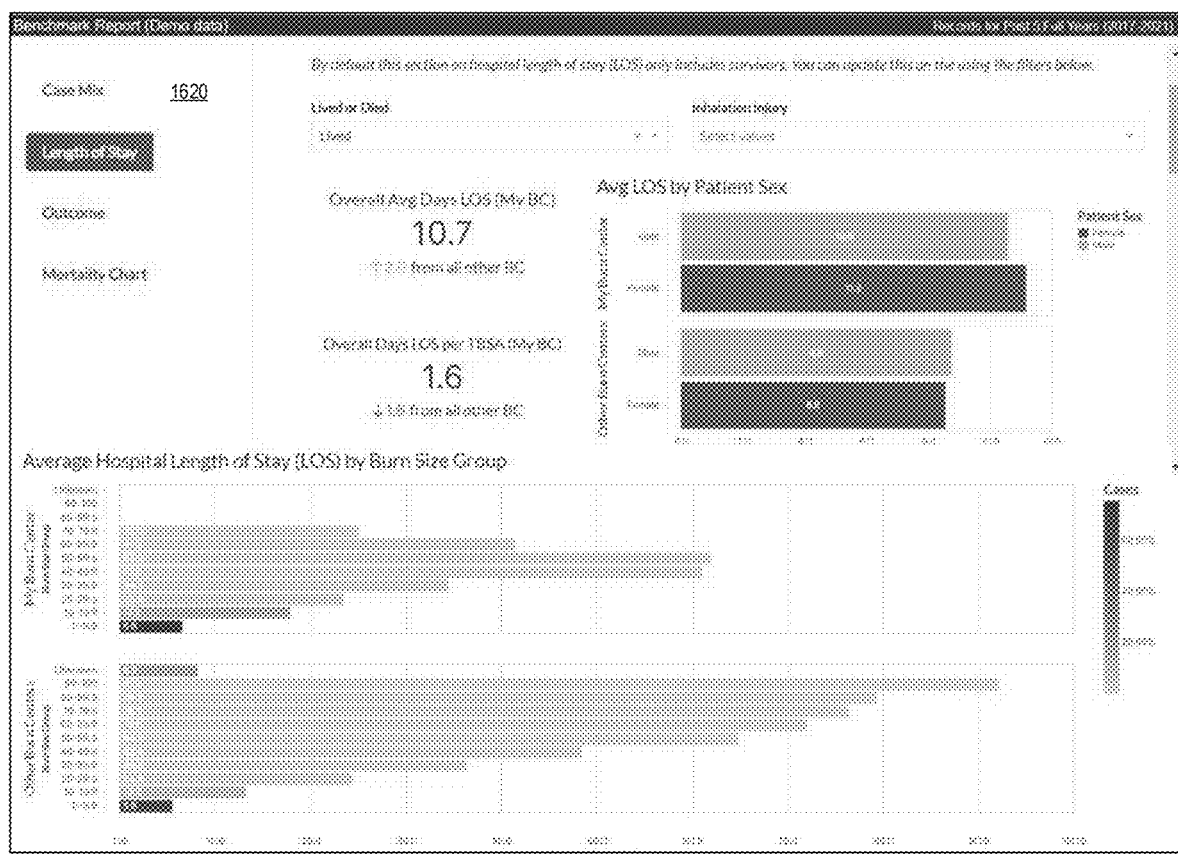

GUI 1620 in FIG. 16C illustrates LOS benchmarking information with one or more graphical and/or visual elements. The GUI 1620 can also include one or more filtering options such as 'Lived or Died' and/or 'Inhalation injury.' One or more other filtering options can be presented and user-selectable to update and change what LOS information is presented in the GUI 1620 and/or how the information is presented. In some implementations, gradient coloring can be used in one or more graphical and/or visual elements to provide insight into a quantity of cases within each category, as shown regarding graphs for 'Average Hospital Length of Stay (LOS) by Burn Size Group.'

Figure 16D:
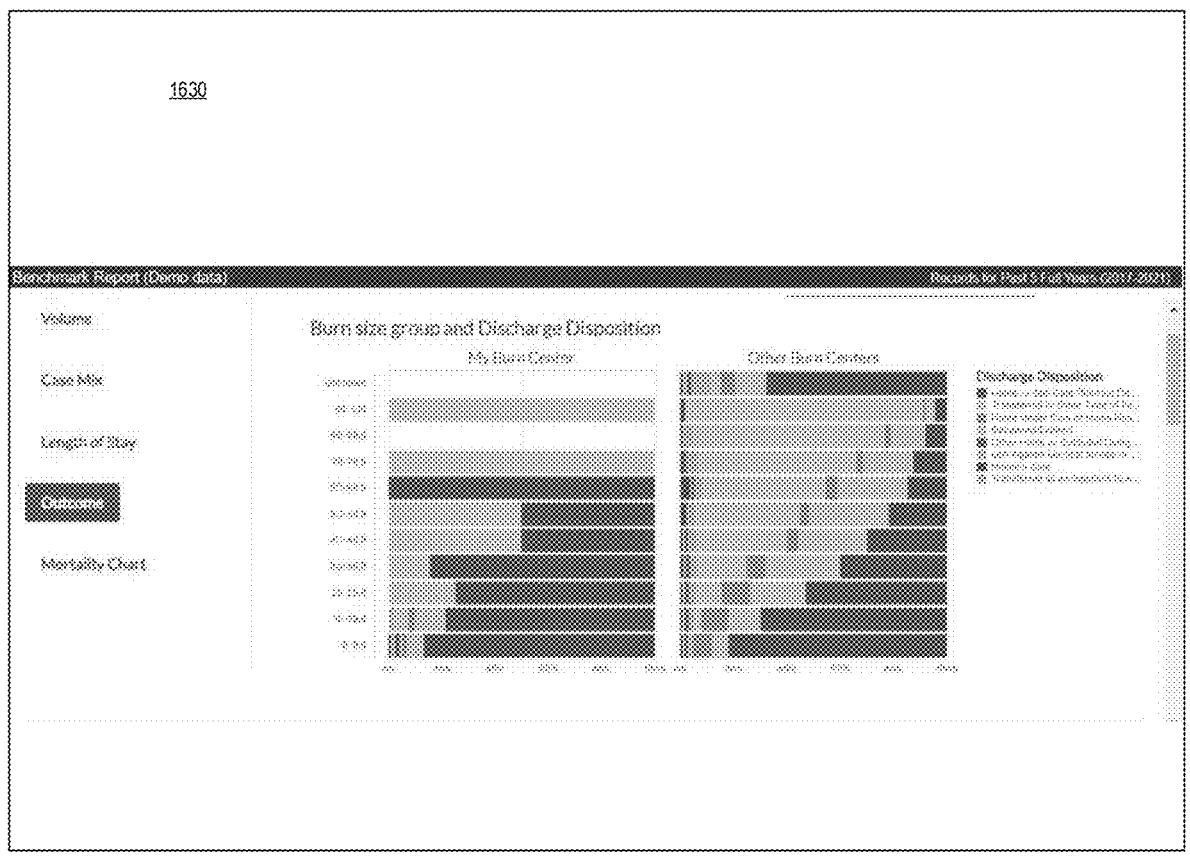

GUI 1630 in FIG. 16D illustrates patient outcome benchmarking information with one or more graphical and/or visual elements. The user can hover over one or more of the graphical and/or visual elements in order to view additional details about that area of interest, as described above. Although the GUI 1630 displays patient outcomes based on burn size group and discharge disposition. Patient outcomes can also be displayed based on one or more other filtering categories, including but not limited to wound closure, or other categories described above.

Figure 16E:

GUI 1640 in FIG. 16E illustrates mortality reporting features. The user can interact with selectable fields, drop-down menus, and other input fields in the GUI 1640 to generate one or more charts. The chart(s) can indicate, for example, mortality rate for cases by age group and/or burn size. Higher mortality rates can be presented in a darker gradient or one or more other visual indicia (e.g., color, patterns). The user can select one or more different groups using filtering options presented in the GUI 1640. The filtering options can include, but are not limited to, admission year, patient sex, inhalation injury, etiology category, and/or ABA region. Once the user makes selections with the filtering options, one or more charts can be presented in the GUI 1640 (or optionally launched in a separate GUI) indicating mortality rates for the particular healthcare center and the other healthcare centers.

Figure 16F:
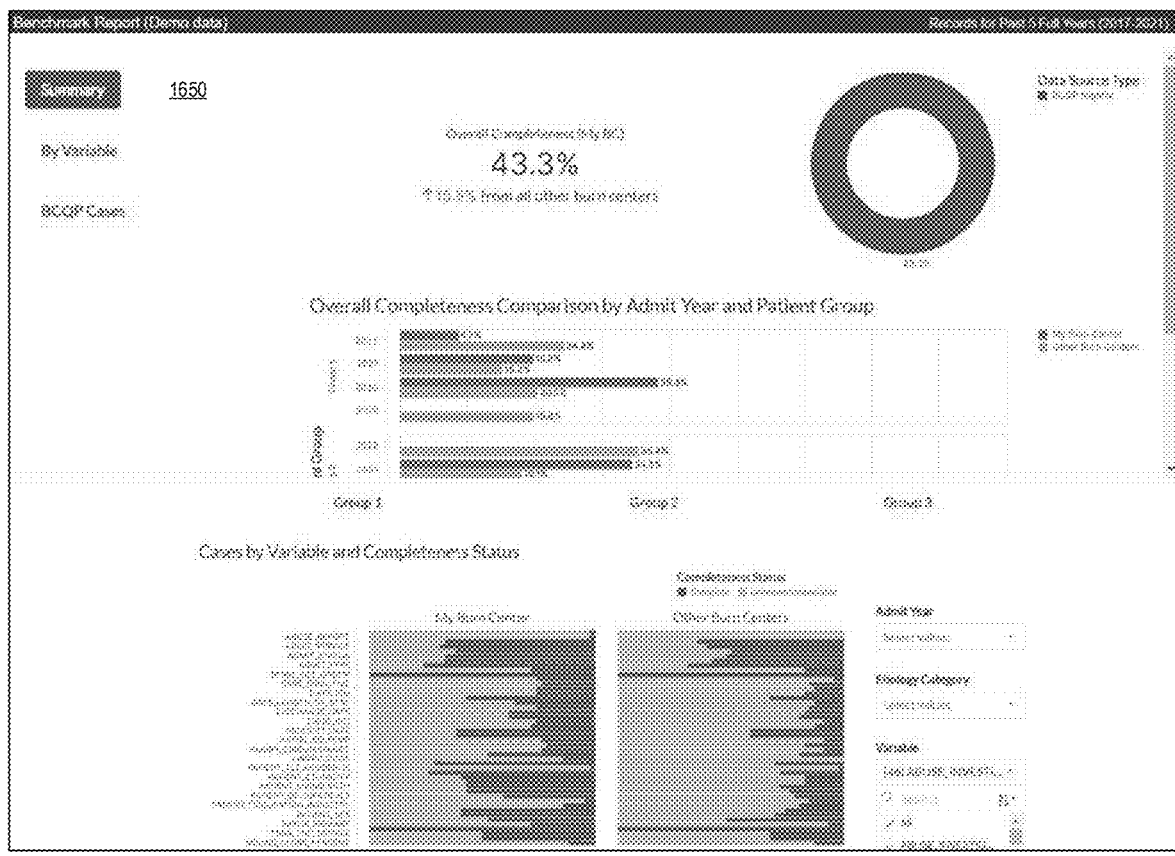

GUI 1650 in FIG. 16F illustrates data quality information for benchmarking. The GUI 1650 can include graphical and/or visual elements indicating an overall completeness summary. These elements may include information such as overall completeness comparison by admission year and patient group, and/or one or more other filtering criteria described throughout this disclosure. The GUI 1650 can also provide overall completeness comparison information for one or more different ABA patient groups (e.g., Group 1, Group 2, Group 3). The reporting described in herein can be broken down for patients in 3 different cohorts: Group 1 can include cases with <10% TBSA, Group 2 can include cases with >=10% TBSA or Inhalation injury or death or surgery, and Group 3 can include cases with >=20% TBSA. Moreover, the data completeness, demographics, outcomes, etc. can be profiled according to these groups in order to help healthcare centers with resource planning at the centers.

Figure 17:
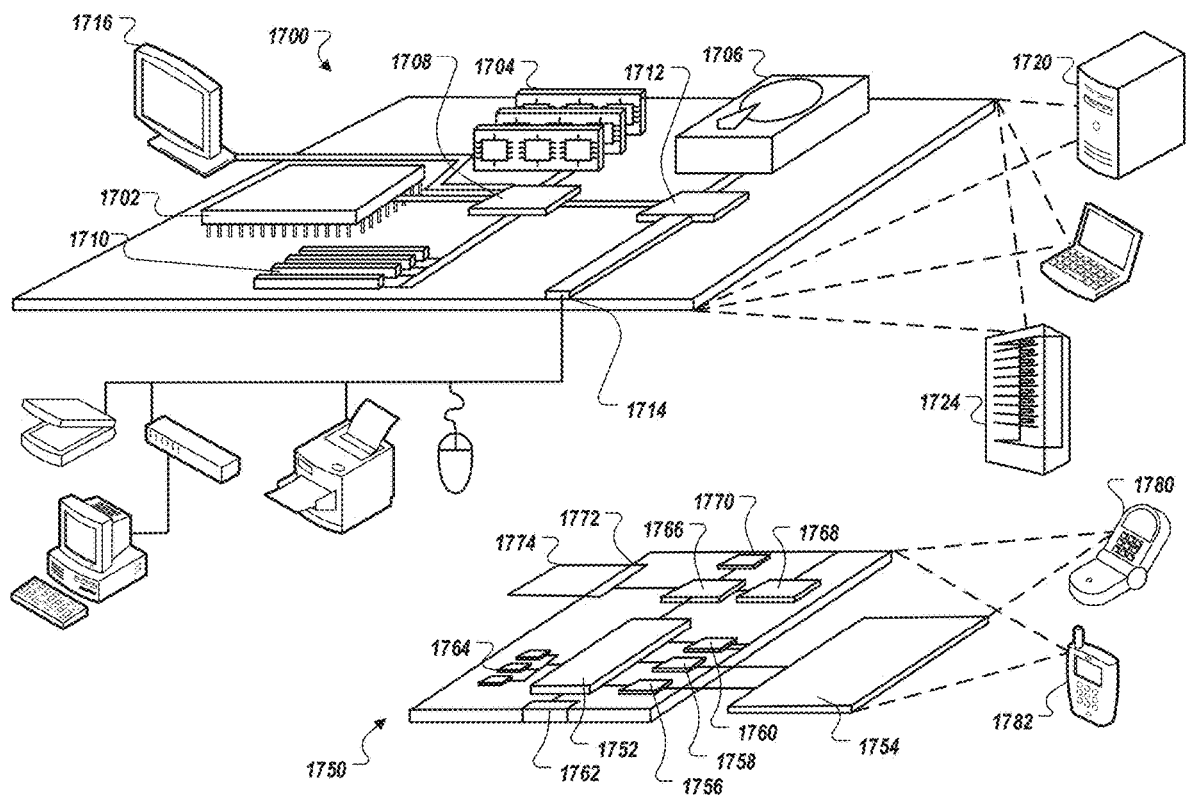
FIG. 17 is a schematic diagram that shows an example of a computing device and a mobile computing device.

FIG. 17 shows an example of a computing device 1700 and an example of a mobile computing device that can be used to implement the techniques described here. The computing device 1700 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 1700 includes a processor 1702, a memory 1704, a storage device 1706, a high-speed interface 1708 connecting to the memory 1704 and multiple high-speed expansion ports 1710, and a low-speed interface 1712 connecting to a low-speed expansion port 1714 and the storage device 1706. Each of the processor 1702, the memory 1704, the storage device 1706, the high-speed interface 1708, the high-speed expansion ports 1710, and the low-speed interface 1712, are interconnected using various busses, and can be mounted on a common motherboard or in other manners as appropriate. The processor 1702 can process instructions for execution within the computing device 1700, including instructions stored in the memory 1704 or on the storage device 1706 to display graphical information for a GUI on an external input/output device, such as a display 1716 coupled to the high-speed interface 1708. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 1704 stores information within the computing device 1700. In some implementations, the memory 1704 is a volatile memory unit or units. In some implementations, the memory 1704 is a non-volatile memory unit or units. The memory 1704 can also be another form of computer-readable medium, such as a magnetic or optical disk.

The storage device 1706 is capable of providing mass storage for the computing device 1700. In some implementations, the storage device 1706 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 1704, the storage device 1706, or memory on the processor 1702.

The high-speed interface 1708 manages bandwidth-intensive operations for the computing device 1700, while the low-speed interface 1712 manages lower bandwidth-intensive operations. Such allocation of functions is exemplary only. In some implementations, the high-speed interface 1708 is coupled to the memory 1704, the display 1716 (e.g., through a graphics processor or accelerator), and to the high-speed expansion ports 1710, which can accept various expansion cards (not shown). In the implementation, the low-speed interface 1712 is coupled to the storage device 1706 and the low-speed expansion port 1714. The low-speed expansion port 1714, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1700 can be implemented in a number of different forms, as shown in the figure. For example, it can be implemented as a standard server 1720, or multiple times in a group of such servers. In addition, it can be implemented in a personal computer such as a laptop computer 1722. It can also be implemented as part of a rack server system 1724. Alternatively, components from the computing device 1700 can be combined with other components in a mobile device (not shown), such as a mobile computing device 1750. Each of such devices can contain one or more of the computing device 1700 and the mobile computing device 1750, and an entire system can be made up of multiple computing devices communicating with each other.

The mobile computing device 1750 includes a processor 1752, a memory 1764, an input/output device such as a display 1754, a communication interface 1766, and a transceiver 1768, among other components. The mobile computing device 1750 can also be provided with a storage device, such as a micro-drive or other device, to provide additional storage. Each of the processor 1752, the memory 1764, the display 1754, the communication interface 1766, and the transceiver 1768, are interconnected using various buses, and several of the components can be mounted on a common motherboard or in other manners as appropriate.

The processor 1752 can execute instructions within the mobile computing device 1750, including instructions stored in the memory 1764. The processor 1752 can be implemented as a chipset of chips that include separate and multiple analog and digital processors. The processor 1752 can provide, for example, for coordination of the other components of the mobile computing device 1750, such as control of user interfaces, applications run by the mobile computing device 1750, and wireless communication by the mobile computing device 1750.

The processor 1752 can communicate with a user through a control interface 1758 and a display interface 1756 coupled to the display 1754. The display 1754 can be, for example, a TFT (Thin-Film-Transistor Liquid Crystal Display) display or an OLED (Organic Light Emitting Diode) display, or other appropriate display technology. The display interface 1756 can comprise appropriate circuitry for driving the display 1754 to present graphical and other information to a user. The control interface 1758 can receive commands from a user and convert them for submission to the processor 1752. In addition, an external interface 1762 can provide communication with the processor 1752, so as to enable near area communication of the mobile computing device 1750 with other devices. The external interface 1762 can provide, for example, for wired communication in some implementations, or for wireless communication in other implementations, and multiple interfaces can also be used.

The memory 1764 stores information within the mobile computing device 1750. The memory 1764 can be implemented as one or more of a computer-readable medium or media, a volatile memory unit or units, or a non-volatile memory unit or units. An expansion memory 1774 can also be provided and connected to the mobile computing device 1750 through an expansion interface 1772, which can include, for example, a SIMM (Single In Line Memory Module) card interface. The expansion memory 1774 can provide extra storage space for the mobile computing device 1750, or can also store applications or other information for the mobile computing device 1750. Specifically, the expansion memory 1774 can include instructions to carry out or supplement the processes described above, and can include secure information also. Thus, for example, the expansion memory 1774 can be provide as a security module for the mobile computing device 1750, and can be programmed with instructions that permit secure use of the mobile computing device 1750. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 1764, the expansion memory 1774, or memory on the processor 1752. In some implementations, the computer program product can be received in a propagated signal, for example, over the transceiver 1768 or the external interface 1762.

The mobile computing device 1750 can communicate wirelessly through the communication interface 1766, which can include digital signal processing circuitry where necessary. The communication interface 1766 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1768 using a radio-frequency. In addition, short-range communication can occur, such as using a Bluetooth, WiFi, or other such transceiver (not shown). In addition, a GPS (Global Positioning System) receiver module 1770 can provide additional navigation- and location-related wireless data to the mobile computing device 1750, which can be used as appropriate by applications running on the mobile computing device 1750.

The mobile computing device 1750 can also communicate audibly using an audio codec 1760, which can receive spoken information from a user and convert it to usable digital information. The audio codec 1760 can likewise generate audible sound for a user, such as through a speaker, e.g., in a handset of the mobile computing device 1750. Such sound can include sound from voice telephone calls, can include recorded sound (e.g., voice messages, music files, etc.) and can also include sound generated by applications operating on the mobile computing device 1750.

The mobile computing device 1750 can be implemented in a number of different forms, as shown in the figure. For example, it can be implemented as a cellular telephone 1780. It can also be implemented as part of a smart-phone 1782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A method for determining outcomes of patients across a plurality of healthcare centers, the method comprising:
   receiving, at a computer system, patient data for patients in a plurality of healthcare centers;
   de-identifying the received data;
   splitting the de-identified data into a training dataset and a testing dataset;
   scaling one or more continuous variables in the training dataset;
   removing a predetermined quantity of sigma outliers from the training dataset;
   imputing missed data in the training dataset;
   returning the training dataset for training;
   training, at the computer system and using the training dataset, a predictive model, wherein the predictive model was trained to predict patient outcomes based on assessing a plurality of patient data for a plurality of patients across the plurality of healthcare centers, wherein the training comprises:
      determining importance values for variables in the training dataset using feature selection modeling techniques; and
      identifying a subset of the variables in the training dataset having respective values that satisfy one or more importance criteria, wherein the subset of the variables has a greater effect on output from the predictive model than other variables in the training dataset; and
   returning, at the computer system, the trained predictive model for runtime use, wherein during the runtime use, the method further comprises:
      generating, based on providing the patient data as input to the trained predictive model, predicted patient outcomes for at least one patient amongst the patients in the plurality of healthcare centers,
      determining, based at least in part on the predicted patient outcomes, at least one care recommendation,
      generating output representative of the predicted patient outcomes and the at least one care recommendation, and
      transmitting the output to a computing device for presentation in a graphical user interface (GUI) display.

2. The method of claim 1, wherein the patients are burn patients.

3. The method of claim 1, wherein the predictive model is a gradient boosted regression model.

4. The method of claim 1, wherein the predictive model is a CatBoost model.

5. The method of claim 1, wherein the predicted patient outcomes include a predicted risk of mortality for the at least one patient.

6. The method of claim 1, wherein the predicted patient outcomes include a predicted length of stay (LOS) for the at least one patient.

7. The method of claim 1, wherein the predicted patient outcomes include a predicted recovery rate for the at least one patient.

8. The method of claim 1, wherein the at least one care recommendation is a patient-specific treatment or care plan.

9. The method of claim 1, wherein the at least one care recommendation is a healthcare center-specific care plan.

10. The method of claim 1, wherein the de-identified data is split into the training dataset and the testing dataset based on a predetermined temporal limitation, the predetermined temporal limitation being a range of years that the received patient data was collected.

11. The method of claim 1, wherein the at least one care recommendation comprises a performance rating for one or more of the plurality of healthcare centers.

12. The method of claim 11, the method further comprising:
   determining and comparing, at the computer system, the performance rating for the one or more of the plurality of healthcare centers; and
   generating, at the computer system, output for presenting the comparison for the one or more of the plurality of healthcare centers.

13. The method of claim 12, wherein comparing, at the computer system, the performance rating for the one or more of the plurality of healthcare centers comprises identifying one or more factors of high performing healthcare centers that are different from low performing healthcare centers.

14. The method of claim 1, wherein the predicted patient outcomes include a predicted risk of mortality for a cohort of the patients.

15. The method of claim 1, wherein the predicted patient outcomes include a predicted length of stay (LOS) for a cohort of the patients.

16. The method of claim 1, wherein the predicted patient outcomes include a predicted recovery rate for a cohort of the patients.

17. The method of claim 1, wherein
   the feature selection modeling techniques comprise CatBoost feature selection modeling techniques, and
   the identified subset of the variables include at least total body surface area (TBSA) and age.

18. The method of claim 17, further comprising:
generating output representative of the identified subset of the variables having respective importance values that exceed the threshold feature importance level; and
transmitting the output representative of the identified subset of the variables to the computing device for presentation in the GUI display.

19. A computing system for determining outcomes of patients across a plurality of healthcare centers, the computing system comprising:
one or more processors; and
one or more storage devices storing instructions that, when executed by the one or more processors, cause the one or more processors to perform operations comprising:
receiving patient data for patients in a plurality of healthcare centers;
de-identifying the received data;
splitting the de-identified data into a training dataset and a testing dataset;
scaling one or more continuous variables in the training dataset;
removing a predetermined quantity of sigma outliers from the training dataset;
imputing missed data in the training dataset;
returning the training dataset for training;
training, using the training dataset, a predictive model, wherein the predictive model was trained to predict patient outcomes based on assessing a plurality of patient data for a plurality of patients across the plurality of healthcare centers, wherein the training comprises:
determining importance values for variables in the training dataset using feature selection modeling techniques;
identifying a subset of the variables in the training dataset having respective values that satisfy one or more importance criteria, wherein the subset of the variables has a greater effect on output from the predictive model than other variables in the training dataset; and
returning the trained predictive model for runtime use, wherein during the runtime use, the operations further comprise:
generating, based on providing the patient data as input to the trained predictive model, predicted patient outcomes for at least one patient amongst the patients in the plurality of healthcare centers,
determining, based at least in part on the predicted patient outcomes, at least one care recommendation,
generating output representative of the predicted patient outcomes and the at least one care recommendation, and
transmitting the output to a computing device for presentation in a graphical user interface (GUI) display.

20. The system of claim 19, wherein:
the patients comprise burn patients, and
the predicted patient outcomes include at least one of (i) a predicted risk of mortality, a predicted LOS, and a predicted recovery rate.

* * * * *